(12) United States Patent
Crystal et al.

(10) Patent No.: US 9,682,133 B2
(45) Date of Patent: Jun. 20, 2017

(54) DISRUPTED ADENOVIRUS-BASED VACCINE AGAINST DRUGS OF ABUSE

(75) Inventors: Ronald G. Crystal, New York, NY (US); Bishnu De, New Hyde Park, NY (US); Martin Hicks, New York, NY (US); Jonathan Rosenberg, Cranbury, NJ (US); Stephen M. Kaminsky, Bronx, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 0 days.

(21) Appl. No.: 13/635,635

(22) PCT Filed: Mar. 17, 2011

(86) PCT No.: PCT/US2011/028815
§ 371 (c)(1),
(2), (4) Date: Sep. 17, 2012

(87) PCT Pub. No.: WO2011/116189
PCT Pub. Date: Sep. 22, 2011

(65) Prior Publication Data
US 2013/0011432 A1   Jan. 10, 2013

Related U.S. Application Data

(60) Provisional application No. 61/373,704, filed on Aug. 13, 2010, provisional application No. 61/314,847, filed on Mar. 17, 2010.

(51) Int. Cl.
*A61K 39/385* (2006.01)
*A61K 39/235* (2006.01)
(Continued)

(52) U.S. Cl.
CPC ........ *A61K 39/0013* (2013.01); *A61K 39/385* (2013.01); *C07K 16/44* (2013.01);
(Continued)

(58) Field of Classification Search
None
See application file for complete search history.

(56) References Cited

U.S. PATENT DOCUMENTS 4,123,431 A   10/1978   Soffer et al.
4,197,237 A   4/1980   Leute et al.
(Continued)

FOREIGN PATENT DOCUMENTS

WO   WO 97/12986 A2   4/1997
WO   WO 97/21451 A1   6/1997
(Continued)

OTHER PUBLICATIONS

Kurachi et al., "Characterization of capsid-modified adenovirus vectors containing heterologous peptides in the fiber knob, protein IX, or hexon," Gene Therapy 14, pp. 266-274 (2007).*
(Continued)

*Primary Examiner* — Janet L Andres
*Assistant Examiner* — M. Franco Salvoza
(74) *Attorney, Agent, or Firm* — Leydig, Voit & Mayer, Ltd.

(57) ABSTRACT

The invention is directed to an adenovirus-antigen conjugate comprising (a) a disrupted adenovirus with a coat protein and (b) an antigen conjugated to the coat protein of the disrupted adenovirus, as well as a conjugate comprising (a) a disrupted adenovirus with a coat protein and (b) an antigen conjugated to the coat protein of the disrupted adenovirus. The invention also provides a method of inducing an immune response against an antigen in a human using the aforementioned conjugates. The invention further provides an adeno-associated viral vector comprising a nucleic acid sequence which encodes an antibody directed against cocaine.

15 Claims, 5 Drawing Sheets

(51) Int. Cl.
A61K 39/00 (2006.01)
C07K 16/44 (2006.01)
(52) U.S. Cl.
CPC ............... A61K 2039/5252 (2013.01); A61K 2039/5254 (2013.01); A61K 2039/5256 (2013.01); A61K 2039/55511 (2013.01); A61K 2039/6075 (2013.01); A61K 2039/62 (2013.01); C12N 2710/10342 (2013.01)

(56) References Cited

U.S. PATENT DOCUMENTS

| | | | |
|---|---|---|---|
| 5,801,030 | A | 9/1998 | McVey et al. |
| 5,837,511 | A | 11/1998 | Falck-Pedersen et al. |
| 5,849,561 | A | 12/1998 | Falck-Pedersen et al. |
| 5,876,727 | A | 3/1999 | Swain et al. |
| 6,232,082 | B1 | 5/2001 | Ennifar et al. |
| 6,932,971 | B2 | 8/2005 | Bachmann et al. |
| 7,094,398 | B1 * | 8/2006 | Lieber et al. ............... 424/93.2 |
| 2003/0091593 | A1 * | 5/2003 | Bachmann et al. ........ 424/204.1 |
| 2004/0059094 | A1 | 3/2004 | Bachmann et al. |
| 2006/0034805 | A1 | 2/2006 | Fang et al. |
| 2007/0243195 | A1 * | 10/2007 | Minke et al. ............. 424/165.1 |
| 2008/0026000 | A1 | 1/2008 | Ennifar et al. |
| 2011/0086063 | A1 | 4/2011 | Crystal et al. |

FOREIGN PATENT DOCUMENTS

| | | |
|---|---|---|
| WO | WO 98/53087 A1 | 11/1998 |
| WO | WO 99/61054 | 12/1999 |
| WO | WO 99/61054 A1 | 12/1999 |
| WO | WO 2004/009116 A2 | 1/2004 |
| WO | WO 2008/140474 A1 | 11/2008 |
| WO | WO 2009/117656 A2 | 9/2009 |
| WO | WO 2009/149252 A1 | 12/2009 |
| WO | WO 2009149252 A1 * | 12/2009 |

OTHER PUBLICATIONS

Ino et al., "Positional linker effects in haptens for cocaine immunopharmacotherapy," Bioorganic & Medicinal Chemistry Letters 17 p. 4280-4283 (2007).*
Curiel et al., "High-Efficiency Gene Transfer Mediated by Adenovirus Coupled to DNA-Polylysine Complexes," Human Gene Therapy 3: 147-154 (1992).*
Vigne et al., "RGD Inclusion in the Hexon Monomer Provides Adenovirus Type 5-Based Vectors with a Fiber Knob-Independent Pathway for Infection," J. Virol. 73(6); 5156 (1999)).*
Molinier-Frenkel et al., "Adenovirus Hexon Protein is a Potent Adjuvant for Activation of a Cellular Immune Response," J. Virol. 76(1): 127 (2002).*
Hoff et al., "Adenovirus-based Transient Expression Systems for Peritoneal Membrane Research," Peritoneal Dialysis International, vol. 26: 547-558 (2006).*
Hodges et al., "Effect of heat and Sodium Dodecyl Sulfate on Solubilization of Proteins before Two-Dimensional Polyacrylamide Gel Electrophoresis," Clin. Chem. 30/12: 2003-2007 (1984).*
European Patent Office, International Preliminary Report on Patentability for International Application No. PCT/US2011/028815 (Sep. 27, 2012).
European Patent Office, International Search Report for International Application No. PCT/US2011/028815 (Aug. 12, 2011).
European Patent Office, Written Opinion for International Application No. PCT/US2011/028815 (Aug. 12, 2011).
Abad et al., "Comparison of a Monoclonal Antibody-Based Enzyme-Linked Immunosorbent Assay and Gas Chromatography for the Determination of Nicotine in Cigarette Smoke Condensates," Anal. Chem., 65: 3227-3231 (1993).
Alberg et al., "Epidemiology of Lung Cancer: Looking to the Future," Journal of Clinical Oncology, 23(14): 3175-3185 (2005).
Amidi et al., "N-Trimethyl chitosan (TMC) Nanoparticles Loaded with Influenza Subunit Antigen for Intranasal Vaccination: Biological Properties and Immunogenicity in a Mouse Model," Vaccine, 25: 144-153 (2007).
Anton et al., "A Novel Bivalent Morphine/Heroin Vaccine that Prevents Relapse to Heroin Addiction in Rodents," Vaccine, 24: 3232-3240 (2006).
Barouch et al., "Adenovirus Vector-Based Vaccines for Human Immunodeficiency Virus Type 1," Human Gene Therapy, 16: 149-156 (2005).
Basak et al., "Modifying Adenoviral Vectors for Use as Gene-Based Cancer Vaccines," Viral Immunology, 17(2): 182-196 (2004).
Beerli et al., "Isolation of Human Monoclonal Antibodies by Mammalian Cell Display," Proc. Natl. Acad. Sci. U.S.A., 105(38): 14336-14341 (2008).
Benuck et al., "Pharmacokinetics of Systemically Administered Cocaine and Locomotor Stimulation in Mice," The Journal of Pharmacology and Experimental Therapeutics, 243(1): 144-149 (1987).
Bhavsar et al., "Polymeric Nano- and Microparticle technologies for Oral Gene Delivery," Expert Opin. Drug Deliv., 4(3): 197-213 (2007).
Bielinska et al., "Mucosal Immunization with a Novel Nanoemulsion-Based Recombinant Anthrax Protective Antigen Vaccine Protects Against Bacillus anthracis Spore Challenge," Infection and Immunity, 75(8): 4020-4029 (2007).
Bonese, et al., "Changes in Heroin Self-Administration by a Rhesus Monkey after Morphine Immunisation," Nature, 252: 708-710 (1974).
Boulanger et al., "Characterization of Adenovirus Protein IX," J. Gen. Virol., 44: 783-800 (1979).
Boulanger, et al., "Comparative Optical Properties of Free and Assembled Hexon Capsomeres of Human Adenovirus Type 2," FEBS Letters, 85(1): 52-56 (1978).
Boyer et al., "Adenovirus-Based Genetic Vaccines for Biodefense," Human Gene Therapy, 16: 157-168 (2005).
Boyer et al., "Comparison of the Efficacy of a Six Genetic Anti-Plaque Vaccine Candidates Against a Lethal Respiratory Tract Challenge with Yersinia pestis," Molecular Therapy, 15(1): S289 (2007).
Byrnes-Blake et al., "Generation of Anti-(+) Methamphetamine Antibodies is not Impeded by (+) Methamphetamine Administration During Active Immunization of Rats," International Immunopharmacology, 1: 329-338 (2001).
Calcedo et al., "Host Immune Responses to Chronic Adenovirus Infections in Human and Nonhuman Primates," Journal of Virology, 83(6): 2623-2631 (2009).
Bunce, C., "Xenova: TA_NIC: Safety, Immunogenicity and Early Sign of Efficacy," 1st UKNSCC [Online] retrieved from the Internet: URL: http://www.uknscc.org/2005_uknscc/speakers/Campbell_bunce.html> on Aug. 10, 2009.
Carrera et al., "Investigations Using Immunization to Attenuate the Psychoactive Effects of Nicotine," Bioorganic & Medicinal Chemistry, 12: 563-570 (2004).
Carrera et al., "Suppression of Psychoactive Effects of Cocaine by Active Immunization," Nature, 378: 727-730 (1995).
Carrera et al., "Evaluation of the Anticocaine Monoclonal Antibody GNC92H2 as an Immunotherapy for Cocaine Overdose," Pharmacol. Biochem. Behav., 81: 709-714 (2005).
Carrera et al., "Cocaine Vaccines: Antibody Protection Against Relapse in a Rat Model," Proc. Nat. Acad. Sci. USA, 97: 6202-6206 (2000).
Carrera et al., "A Second-Generation Vaccine Protects Against the Psychoactive Effects of Cocaine," Proc. Natl. Acad. Sci USA, 98: 1988-1992 (2001).
Castro et al., "Nicotine Antibody Production: Comparison of Two Nicotine Conjugates in Different Animal Species," Biochemical and Biophysical Research Communications, 67(2): 583-589 (1975).
Castro et al., "Nicotine Antibodies: Comparison of Ligand Specificities of Antibodies Produced Against Two Nicotine Conjugates," Eur. J. Biochem., 104: 331-340 (1980).

(56) References Cited

OTHER PUBLICATIONS

Cerny et al., "Anti-Nicotine Abuse Vaccines in the Pipeline: An Update," *Expert Opinion on Investigational Drugs*, 17(5): 691-696 (2008).
Cerny et al., "Preclinical Development of a Vaccine 'Against Smoking,'" *Onkologie*, 25: 406-411 (2002).
Cerny, T., "Anti-Nicotine Vaccination: Where Are We'?," *Recent Results Cancer Res.*, 166: 167-175 (2005).
Chavdarian et al., "Bridged Nicotines. Synthesis of cis-2,3,3a,4,5,9b-Hexahydro-1-methyl-1*H*-pyrrolo[2,3-*f*]quinoline," *J. Org. Chem.*, 48: 492-494 (1983).
Chawla et al., "Adenovirus-vectored Vaccines," *Expert Opinion on Therapeutic Patents*, 18(3): 293-307 (Mar. 2008).
Chirmule et al., "Immune Responses to Adenovirus and Adeno-Associated Virus in Humans," *Gene Therapy*, 6: 1574-1583 (1999).
Church et al., "free-Radical Chemistry of Cigarette Smoke and Its Toxilogical Implications," *Environmental Health Perspectives*, 64: 111-126 (1985).
Cohen, J., "Promising AIDS Vaccine's Failure Leaves Field Reeling," *Science*, 318: 28-29 (2007).
Cornuz et al., "A Vaccine Against Nicotine for Smoking Cessation: A Randomized Controlled Trial," *PLoS. One.*, 3(6): e2547 (2008).
Crystal et al., "Administration of an Adenovirus Containing the Human *CFTR* cDNA to the Respiratory Tract of Individuals with Cystic Fibrosis," *Nature Genetics*, 8: 42-51 (1994).
Cui et al., "Microparticles and Nanoparticles as Delivery Systems for DNA Vaccines," *Critical Reviews in Therapeutic Drug Carrier Systems*, 20(2&3): 103-137 (2003).
Cutler et al., "Cytokine Therapy," *Ann. NY Acad. Sci.*, 1056: 16-29 (2005).
de Villiers et al., "Active Immunization Against Nicotine Suppresses Nicotine-Induced Dopamine Release in the Rat Nucleus accumbens Shell," *Respiration*, 69: 247-253 (2002).
Defer et al., "Human Adenovirus-Host Cell Interactions: Comparative Study with Members of Subgroups B and C," *Journal of Virology*, 64(8): 3661-3673 (1990).
Degenhardt et al., "Toward a Global View of Alcohol, Tobacco, Cannabis, and Cocaine Use: Findings from the WHO World Mental Health Surveys," *PLoS. Medicine*, 5(7): e141 (2008).
Duryee et al., "Immune Responses to Methamphetamine by Active Immunization with Peptide-Based, Molecular Adjuvant-Containing Vaccines," *Vaccine*, 27: 2981-2988 (2009).
Elmore et al., "A Computational Study of Nicotine Conformations in the Gas Phase and in Water," *J. Org. Chem.*, 65: 742-747 (2000).
European Patent Office, International Preliminary Report on Patentability for International Application No. PCT/US2009/046248 (Dec. 6, 2010).
European Patent Office, International Search Report for International Application No. PCT/US2009/046248 (Sep. 9, 2009).
European Patent Office, Written Opinion for International Application No. PCT/US2009/046248 (Sep. 9, 2009).
Evans et al., "Arterial and Venous Cocaine Plasma Concentrations in Humans: Relationship to Route of Administration, Cardiovascular Effects and Subjective Effects," *The Journal of Pharmacology and Experimental Therapeutics*, 279(3): 1345-1356 (1996).
Evans et al., "Pharmacokinetics of Intravenous Cocaine Across the Menstrual Cycle in Rhesus Monkeys," *Neuropsychopharmacology*, 29: 1889-1900 (2004).
Evans et al., "Pharmacokinetics of Repeated Doses of Intravenous Cocaine Across the Menstraul Cycle in Rhesus Monkey," *Pharmacology, Biochemistry and Behavior*, 83: 56-66 (2006).
Fang et al., "Stable Antibody Expression at Therapeutic Levels Using The 2A Peptide" *Nature Biotechnology*, 23(5): 584-590 (2005).
Farina et al., "Replication-Defective Vector Based on a Chimpanzee Adenovirus," *Journal of Virology*, 75(23): 11603-11613 (2001).
Fifis et al., "Short Peptide Sequences Containing MHC Class I and/or II Epitopes Linked to Nano-Beads Induce Strong Immunity and Inhibition of Growth of Antigen-Specific Tumour Challenge in Mice," *Vaccine*, 23: 258-266 (2004).
Fiore et al., "Clinical Practice Guideline: Treating Tobacco Use and Dependence," *U.S. Dept. of Health and Human Services, Public Health Service*, (2000).
Fiore, M., "Treating Tobacco Use and Dependence: An Introduction to the US Public Health Service Clinical Praactice Guideline," *Respiratory Care*, 45(10): 1196-1199 (2000).
Fox et al., "Efficacy of a Therapeutic Cocaine Vaccine in Rodent Models," *Nature Medicine*, 2(10): 1129-1132 (1996).
Garcea et al., "Virus-Like Particles as Vaccines and Vessels for the Delivery of Small Molecules," *Current Opinion in Biotechnology*, 15: 513-517 (2004).
Gard et al., "Immunization with Inactivated Measles Virus Vaccine," *Arch. Gesamte Virusforsch.*, 16: 315-323 (1965).
Gell et al., "Studies on Hypersensitivity: IV. The Relationship Between Contact and Delayed Sensitivity: A Study on the Specificity of Cellular Immune Reactions," *J. Exp. Med.*, 113: 571-585 (1961).
Glassco et al., "Synthetsis, Optical Resolution, Absolute Configuration, and Preliminary Pharmacology of (+)- and (−)-*cis*-2,3,3a,4,5,9b-Hexahydro-1-methyl-1*H*-pyrrolo-[3,2-*h*]isoquinoline, a Structural Analog of Nicotine," *J. Med. Chem.*, 36: 3381-3385 (1993).
Good et al., "Preparation of Hapten-Modified Protein Antigens," *Selected Methods in Cellular Immunology*: 343-350, (1980).
Greber et al., "The Role of the Nuclear Pore Complex in Adenovirus DNA Entry," *The EMBO Journal*, 16(19): 5998-6007 (1997).
Hackett et al., "Antivector and Antitransgene Host Responses in Gene Therapy," *Current Opinion in Molecular Therapy*, 2(4): 376-382 (2000).
Hackett et al., "Adenovirus Vectors for Gene Therapy," *Gene Therapy: Therapeutic Mechanisms and Strategies*, Second Edition: 17-40, (2004).
Hardin et al., Pharmacodynamics of a Monoclonal Antiphencyclidine Fab with Broad Selectivity for Phencyclidine-Like Drugs, *J. Pharmacol. Exp. Ther.*, 285: 1113-1122 (1998).
Harvey et al., "Variability of Human Systemic Humoral Immune Responses to Adenovirus Gene Transfer Vectors Administered to Different Organs," *Journal of Virology*, 73(8): 6729-6742 (1999).
Harvey et al., "Cellular Immune Responses of Healthy Individuals to Intradermal Administration of an E1⁻ E3⁻ Adenovirus Gene Transfer Vector," *Human Gene Therapy*, 10: 2823-2837 (1999).
Harvey et al., "Airway Epithelial CFTR mRNA Expression in Cystic Fibrosis patients after Repetitive Administration of a Recombinant Adenovirus," *The Journal of Clinical Investigation*, 104(9): 1245-1255 (1999).
Harvey et al., "Safety of Local Delivery of Low- and Intermediate-Dose Adenovirus Gene Transfer Vectors to Individuals with a Spectrum of Morbid Conditions," *Human Gene Therapy*, 13: 15-63 (2002).
Hashimoto et al., "Induction of Protective Immunity to Anthrax Lethal Toxin with a Nonhuman Primate Adenovirus-Based Vaccine in the Presence of Preexisting Anti-Human Adenovirus Immunity," *Infection and Immunity*, 73(10): 6885-6891 (2005).
Hatsukami et al., "Safety and Immunogenicity of a Nicotine Conjugate Vaccine in Current Smokers," *Clinical Pharmacology & Therapeutics*, 78(5): 456-467 (2005).
Hieda et al., "Vaccination Against Nicotine During Continued Nicotine Administration in Rats: Immunogenicity of the Vaccine and Effects on Nicotine Distribution to Brain," *International Journal of Immunopharmacology*, 22: 809-819 (2000).
Hieda et al., "Active Immunization Alters the Plasma Nicotine Concentration in Rats," *The Journal of Pharmacology and Experimental Therapeutics*, 283(3): 1076-1081 (1997).
Hieda et al., "Immunization of Rats Reduces Nicotine Distribution to Brain," *Psychopharmacology*, 143: 150-157 (1999).
Hildinger et al., "Hybrid Vectors Based on Adeno-Associated Virus Serotypes 2 and 5 for Muscle-Directed Gene Transfer," *Journal of Virology*, 75(13): 6199-6203 (2001).
Hirschowitz et al., "Adenovirus-Mediated Expression of Melanoma Antigen gp75 as Immunotherapy for Metastic Melanoma," *Gene Therapy*, 5: 975-983 (1998).
Hylkema et al., "Tobacco Use in Relation to COPD and Asthma," *European Respiratory Journal*, 29: 438-445 (2007).

(56) References Cited

OTHER PUBLICATIONS

Isomura et al., "An Immunotherapeutic Program for the Treatment of Nicotine Addiction: Hapten Design and Synthesis," *J. Org. Chem.*, 66(12): 4115-4121 (2001).
Jegerlehner et al., "Regulation of IgG Antibody Responses by Epitope Density and CD21-Mediated Costimulation," *Eur. J. Immunol.*, 32: 3305-3314 (2002).
Jiang et al., "Novel Chitosan Derivative Nanoparticles Enhance the Immunogenicity of a DNA Vaccine Encoding Hepatitis B Virus Core Antigen in Mice," *The Journal of Gene Medicine*, 9: 253-264 (2007).
Jooss et al., "Immunity to Adenovirus and Adeno-Associated Viral Vectors: Implications for Gene Therapy," *Gene Therapy*, 10: 955-963 (2003).
Kantak et al., "Evaluation of Anti-Cocaine Antibodies and a Cocaine Vaccine in a Rat Self-Administration Model," *Psychopharmacology* 148: 251-262 (2000).
Kantor et al., "Studies on Artificial Antigens: I. Antigenicity of DNP-Polylysine and DNP Copolymer of Lysine and Glutamic Acid in Guinea Pigs," *J. Exp. Med.*, 117: 55-69 (1963).
Keyler et al., "Enhanced Immunogenicity of a Bivalent Nicotine Vaccine," *International Immunopharmacology*, 8: 1589-1594 (2008).
Kikuchi et al., "Dendritic Cells Modified to Express CD40 Ligand Elicit Therapeutic Immunity Against Preexisting Murine Turmors," *Blood*, 96(1): 91-99 (2000).
Kikuchi et al., "Dendritic Cells Genetically Modified to Express CD40 Ligand and Pulsed with Antigen Can Initiate Antigen-Specific Humoral Immunity Independent of CD4+ T Cells," *Nature Medicine*, 6(10): 1154-1159 (2000).
Killian et al., "Effects of Passive Immunization Against Morphine on Heroin Self-Administration," *Pharmacology, Biochemistry & Behavior*, 9: 347-352 (1978).
Kinsey et al., "Anti-Drug Vaccines to Treat Substance Abuse," *Immunology and Cell Biology*, 87: 309-314 (2009).
Kleber et al., "Treatment of Patients with Substance Abuse Use Disorders, Second Edition" *Am. J. Psych.*, 164(4 Suppl.): 5-123 (2007).
Koob et al., "Drug Abuse: Hedonic Homeostatic Dysregulation," *Science*, 278: 52-58 (1997).
Krause et al., "Epitopes Expressed in Different Adenovirus Capsid Proteins Induce Different Levels of Epitope-Specific Immunity," *Journal of Virology* 80(11): 5523-5530 (2006).
Langone et al., "Nicotine and Its Matabolites. Radioimmunoassays for Nicotine and Cotinine," *Biochemistry*, 12(24): 5025-5030 (1973).
Langone et al., "Radioimmunoassay of Nicotine, Cotinine, and y-(3-Pyridyl)-y-oxo-N-methylbutyramide," *Methods in Enzymology*, 84: 628-640 (1982).
Le Houezec, J., "Why a Nicotine Vaccine?" *Clinical Pharmacology & Therapeutics*, 78: 453-455 (2005).
Leopold et al., "Fluorescent Virions: Dynamic Tracking of the Pathway of Adenoviral Gene Transfer Vectors in Living Cells," *Human Gene Therapy*, 9: 367-378 (1998).
Leopold et al., "Dynein- and Microtubule-Mediated Translocation of Adenovirus Serotype 5 Occurs after Endosomal Lysis," *Human Gene Therapy*, 11: 151-165 (2000).
Leopold et al., "Neutralized Adenovirus-Immune Complexes Can Mediate Effective Gene Transfer via an Fc Receptor-Dependent Infection Pathway," *Journal of Virology*, 80(20): 10237-10247 (2006).
Leopold, P., "Microtubule-Dependent Motility uring Intracellular Trafficking of Vector Genome to the Nucleus: Subcellular Mimicry in Virology and Nanoengineering," *Nanotechnology in Biology and Medicine*: 34:1-17, (2007).
Lindblom et al., "Active Immunization Against Nicotine Prevents Reinstatement of Nicotine-Seeking Behavior in Rats," *Respiration*, 69: 254-260 (2002).

Mack et al., "Circumvention of Anti-Adenovirus Neutralizing Immunity by Administration of an Adenoviral Vector of an Alternate Serotype," *Human Gene Therapy*, 8: 99-109 (1997).
Maizel et al., "The Polypeptides of Adenovirus," *Virology*, 36: 126-136 (1968).
Malin et al., "Passive Immunization Against Nicotine Prevents Nicotine Alleviation of Nicotine Abstinence Syndrome," *Pharmacology, Biochemistry and Behavior*, 68: 87-92 (2001).
Malin, D., "Nicotine Dependence Studies with a Laboratory Model," *Pharmacology, Biochemistry and Behavior*, 70: 551-559 (2001).
Martell et al., "Cocaine Vaccine for the Treatment of Cocaine Dependence in Methadone-Maintained Patients: A Randomized, Double-Blind, Placebo-Controlled Efficacy Trial," *Arch. Gen. Psychiatry*, 66(10): 1116-1123 (2009).
Mastrangeli et al., "'Sero-Switch' Adenovirus-Mediated In Vivo Gene Transfer: Circumvention of Anti-Adenovirus Humoral Immune Defenses Against Repeat Adenovirus Vector Administration by Changing the Adenovirus Serotype," *Human Gene Therapy*, 7: 79-87 (1996).
Matsushita et al., "Conjugate of Bovine Serum Albumin with Nicotine," *Biochem. Biochemical and Biophysical Research Communications*, 57: 1006-1010 (1974).
Maurer et al., "A Therapeutic Vaccine for Nicotine Dependence: Preclinical Efficacy, and Phase I Safety and Immunogenicity," *Eur. J. Immunol.*, 35: 2031-2040 (2005).
Maurer et al., "Vaccine Against Nicotine: An Emerging Therapy for Tobacco Dependence," *Expert Opinion on Investigational Drugs*, 16(11): 1775-1783 (Nov. 2007).
McKenzie et al., "Identification and Characterization of Single Chain Anti-Cocaine Catalytic Antibodies," *J.Mol. Biol.*, 365: 722-731 (2007).
Meijler et al., "A New Strategy for Improved Nicotine Vaccines Using Conformationally Contrained haptens," *J. Am. Chem. Soc.*, 125: 7164-7165 (2003).
Mets et al., "A Catalytic Antibody Against Cocaine Prevents Cocaine's Reinforcing and Toxic Effects in Rats," *Proc. Natl. Acad. Sci.*, 95: 10176-10181 (1998).
Minigo et al., "Poly-$_L$-lysine-coated nanoparticles: A potent delivery system to enhance DNA vaccine efficacy," *Vaccine*, 25: 1316-1327 (2007).
Mittereder et al., "Evaluation of the Concentration and Bioactivity of Adenovirus Vectors for Gene Therapy," *Journal of Virology*, 70(11): 7498-7509 (1996).
Miyazawa et al., "Fiber Swap between Adenovirus Subgroups B and C Alters Intracellular Trafficking of Adenovirus Gene Transfer Vectors," *Journal of Virology*, 73(7): 6056-6065 (1999).
Miyazawa et al., "Adenovirus Serotype 7 Retention in a Late Endosomal Compartment prior to Cytosol Escape is Modulated by Fiber Protein," *Journal of Virology*, 75(3): 1387-1400 (2001).
Molinier-Frenkel et al., "Adenovirus Hexon Protein is a Potent Adjuvant for Activation of a Cellular Immune Response," *Journal of Virology*, 76(1): 127-135 (2002).
Moreno et al., "A Critical Evaluation of a Nicotine Vaccine within a Self-Administration Behavioral Model," *Molecular Pharmaceutics*, 7: 431-441 (2010).
Mottram et al., "Type 1 and 2 Immunity Following Vaccination is Influenced by Nanoparticle Size: Formulation of a Model Vaccine for Respiratory Syncytial Virus," *Molecular Pharmaceutics*, 4(1): 73-84 (2007).
Muller, R., "Determination of Affinity and Specificity of Anti-Hapten Antibodies by Competetive Radioimmunoassay," *Methods in Enzymology*, 92: 589-601 (1983).
Mumper et al., "Genetic immunization by jet injection of targeted pDNA-coated nanoparticles," *Methods*, 31: 255-262 (2003).
Nermut, "The Architecture of Adenoviruses", pp. 5-34, in H. S. Ginsberg (ed.), *The Adenoviruses*, Plenum Press, New York, N.Y. (1984).
Ninalga et al., "CpG Oligonucleotide Therapy Cures Subcutaneous and Orthotopic Tumors and Evokes Protective Immunity in Murine Bladder Cancer," *J. Immunother.*, 28(1): 20-27 (2005).

(56) References Cited

OTHER PUBLICATIONS

Noguchi et al., "Conjugate of Nicotine and Cotinine to Bovine Serum Albumin," *Biochemical and Biophysical Research Communications*,, 83(1): 83-86 (1978).

Norman et al., "A Chimeric Human/Murine Antococaine Monoclonal Antibody Inhibits the Distribution of Cocaine to the Brain in Mice," *The Journal of Pharmacology and Experimental Therapeutics*, 320(1): 145-153 (2007).

Ochoa et al., "Protective immunity of biodegradable nanoparticle-based vaccine against an experimental challenge with *Salmonella enteritidis* in mice," *Vaccine*, 25: 4410-4419 (2007).

Pagona et al., "Carbon Nanotubes: Materials for Medicinal Chemistry and Biotechnological Applications," *Current Medicinal Chemistry*, 13: 1789-1798 (2006).

Pentel et al., "A Nicotine Conjugate Vaccine Reduces Nicotine Distribution to Brain and Attenuates Its Behavioral and Cardiovascular Effects in Rats," *Pharmacology Biochemistry and Behavior*, 65: 191-198 (2000).

Plikaytis et al., "Comparisons of Standard Curve-Fitting Methods to Quantitate *Neisseria meningitidis* Group A Polysaccharide Antibody Levels by Enzyme-Linked Immunosorbent Assay," *Journal of Clinical Microbiology*, 29(7): 1439-1446 (1991).

Proksch et al., "Anti-Phencyclidine Monoclonal Antibodies Provide Long-Term Reductions in Brain Phencyclidine Concentrations during Chronic Phencyclidine Administration in Rats," *The Journal of Pharmacology and Experimental Therapeutics*, 292: 831-837 (2000).

Redwan et al., "Expression and Characterization of a Humanized Cocaine-Binding Antibody," *Biotechnology and Bioengineering*, 82(5): 612-8 (2003).

Ribeiro et al., "PLGA-dendron nanoparticles enhance immunogenicity but not lethal antibody production of a DNA vaccine against anthrax in mice," *International Journal of Pharmaceutics*, 331: 228-232 (2007).

Roiko et al., "Combined Active and Passive Immunization Enhances the Efficacy of Immunotherapy Against Nicotine in Rats," *The Journal of Pharmacology and Experimental Therapeutics*, 325(3): 985-993 (2008).

Rosenfeld et al., "In Vivo Transfer of the Human Cystic Fibrosis Transmembrane Conductance Regulator Gene to the Airway Epithelium," *Cell*, 68: 143-155 (1992).

Ross et al., "Pharmacotherapy of Addictive Disorders," *Clinical Nueropharmacology*, 32(5): 277-289 (2009).

Roy et al., "Creation of a panel of vectors based on ape adenovirus isolates," *The Journal of Gene Medicine*, 13: 17-25 (2011).

Russell et al., "The Preparation and Properties of Adenovirus Cores," *Journal of General Virology*, II: 35-46 (1971).

Salk et al., "Control of Influenza and Poliomyelitis with Killed Virus Vaccines," *Science*, 195: 834-847 (1977).

Sanderson et al., "Immunization to nicotine with a peptide-based vaccine composed of a conformationally biased agonist of C5a as a molecular adjuvant," *International Immunopharmacology*, 3(1): 137-146 (2003).

Sondhi et al., "Enhanced Survival of the LINCL Mouse Following CLN2 Gene Transfer Using the rh.10 Rhesus Macaque-derived Adeno-associated Virus Vector," *Molecular Therapy*, 15(3): 481-491 (2007).

Stewart, "Pathways to relapse: the neurobiology of drug- and stress-induced relapse to drug-taking," *Journal of Psychiatry and Neuroscience*, 25(2): 125-136 (2000).

Takahashi et al., "Quantitation of adenovirus type 5 empty capsids," *Analytical Biochemistry*, 349: 208-217 (2006).

Tertilt et al., "Co-Administration of an Adenovirus Encoding the B Cell Stimulating Factor BAFF with Heat-Inactivated *Pseudomonas aeruginosa* Leads to Increased Anti-*pseudomonal* Humoral Immunity," *Molecular Therapy*, 9(Suppl. 1): S210 (2004).

Tuncok et al., "Inhibition of Nicotine-Induced Seizures in Rats by Combining Vaccination Against Nicotine With Chronic Nicotine Infusion," *Experimental and Clinical Psychopharmacology*, 9: 228-234 (2001).

Vincent et al., "Rapid Assessment of Adenovirus Serum Neutralizing Antibody Titer Based on Quantitative, Morphometric Evaluation of Capsid Binding and Intracellular Trafficking: Population Analysis of Adenovirus Capsid Association with Cells is Predictive of Adenovirus Infectivity," *Journal of Virology*, 75(3): 1516-1521 (2001).

Volkow et al., "Relationship Between Subjective Effects of Cocaine and Dopamine Transporter Occupancy," *Nature*, 386: 827-830 (1997).

Votaw et al., "Measurement of Dopamine Transporter Occupancy for Multiple Injections of Cocaine Using a Single Injection of [F-18]FECNT," *Synapse*, 44: 203-210 (2002).

Waldmann, T., "The biology of interleukin-2 and interleukin-15: implications for cancer therapy and vaccine design," *Nature Reviews Immunology*, 6: 595-601 (2006).

Wee et al., "$\alpha$1-Noradrenergic System Role in Increased Motivation for Cocaine Intake in Rats with Prolonged Access," *European Neuropsychopharmacology*, 18: 303-311 (2008).

Wold et al., "Immune Responses to Adenoviruses: Viral Evasion Mechanisms and their Implications for the Clinic," *Current Opinion in Immunology*, 11: 380-386 (1999).

Worgall et al., "Selective Expansion of Alveolar Macrophages In Vivo by Adenovirus-Mediated Transfer of the Murine Granulocyte-Macrophage Colony-Stimulating Factor cDNA," *Blood*, 93(2): 655-666 (1999).

Worgall et al., "Protection against Pulmonary Infection with *Pseudomonas aeruginosa* following Immunization with *P. aeruginosa*-Pulsed Dendritic Cells," *Infection and Immunity*, 69(7): 4521-4527 (2001).

Worgall et al., "Augmentation of pulmonary host defense against *Pseudomonas* by Fc$\gamma$RIIA cDNA transfer to the respiratory epithelium," *The Journal of Clinical Investigation*, 104(4): 409-418 (1999).

Worgall et al., "Protection against *P. aeruginosa* with an adenovirus vector containing an OprF epitope in the capsid," *The Journal of Clinical Investigation*, 115(5): 1281-1289 (2005).

Worgall et al., "Modification to the Capsid of the Adenovirus Vector That Enhances Dendritic Cell Infection and Transgene-Specific Cellular Immune Responses," *Journal of Virology*, 78(5): 2572-2580 (2004).

Xia et al., "Combinational adenovirus-mediated gene therapy and dendritic cell vaccine in combating well-established tumors," *Cell Research*, 16: 241-259 (2006).

Yamada et al., "Novel and Cell Type-specific Gene-Drug Delivery System Using Surface Engineered Hepatitis B Virus Nano-particles," *Current Drug Targets—Infectious Disorders*, 4: 163-167 (2004).

Zhou et al., "Therapeutic potential of adenovirus as a vaccine vector for chronic virus infections," *Expert Opinion on Biological Therapy*, 6(1): 63-72 (2006).

Bayer et al., "Vaccination with an Adenoviral Vector That Encodes and Displays a Retroviral Antigen Induces Improved Neutralizing Antibody and CD4+ T-Cell Responses and Confers Enhanced Protection", *Journal of Virology*, 84(4): 1967-1976 (2009).

Hoff et al, "Adenovirus-Based Transient Expression Systems for Peritoneal Membrane Research", *Peritoneal Dialysis International*, 26(5): 547-558 (2006).

Vigne et al., "RGD Inclusion in the Hexon Monomer Provides Adenovirus Type 5-Based Vectors with a Fiber Knob-Independent Pathway for Infection", *Journal of Virology, American Society for Microbiology*, 73(6): 5156-5161 (1999).

\* cited by examiner

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 1

Asn Phe Phe Ser Ser Lys Lys Lys Lys Arg Glu Ala Thr Ala
1               5                   10                  15

<210> SEQ ID NO 2
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 2

Phe Ser Tyr Ile Ala Gln Glu Gly Ser Gly Ser Gly Ser Gly
1               5                   10                  15

Ser Lys Lys Lys Lys Lys Lys Lys
            20
```

DISRUPTED ADENOVIRUS-BASED VACCINE AGAINST DRUGS OF ABUSE

CROSS-REFERENCE TO RELATED APPLICATIONS

This patent application claims the benefit of U.S. Provisional Patent Application No. 61/314,847, filed Mar. 17, 2010, and U.S. Provisional Patent Application No. 61/373,704, filed Aug. 13, 2010, which are incorporated by reference.

STATEMENT REGARDING FEDERALLY SPONSORED RESEARCH AND DEVELOPMENT

This invention was made with Government support under Grant Numbers DA025305, DA028847, and SN271200 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 996 Byte ASCII (Text) file named "711083_ST25.TXT," created on Sep. 17, 2012.

BACKGROUND OF THE INVENTION

Addiction to drugs is a major problem worldwide. Although a variety of strategies are in use to prevent and treat drug addiction, major economic and social costs are associated with drug addiction.

Despite decades of effort focused upon developing strategies to prevent and treat drug addiction, very little success has been achieved. In the case of nicotine addiction, active behavioral interventions such as individual or group counseling or cognitive therapy alone or in combination with drug therapies such as nicotine replacement therapy (e.g., via chewing gum, transdermal patches, nasal sprays, inhalers, or lozenges), bupropion (ZYBAN™), and varenicline (CHANTIX™), have improved the rates of achieving successful quitting, but the success rates remain only 1.5- to 2.0-fold over placebo, with long term (1 yr) smoking cessation rates of only 5 to 20%. There has been a similar lack of success in the treatment of cocaine addition, and there are no small molecule, monoclonal antibody, or enzyme therapies that have been approved for treatment of cocaine addiction.

Vaccines represent another strategy to prevent and treat drug addiction, and results with vaccines against nicotine and other small molecules such as cocaine and morphine/heroin have been described (Carrera et al., *Proc. Natl. Acad. Sci USA*, 98: 1988-1992 (2001); Anton and Leff, *Vaccine*, 24: 3232-3240 (2006); Carrera et al., *Nature*, 378: 727-730 (1995); Hatsukami et al., *Clin. Pharmacol. Ther.*, 78: 456-467 (2005); Maurer et al., *Eur. J. Immunol.*, 35: 2031-2040 (2005)). A major hurdle in the development of effective vaccines is that most addictive drugs, like most small molecules, are poor immunogens. The immunogenicity of addictive drugs can be enhanced by chemically conjugating a drug (or analog thereof) to a larger molecule, such as a protein, and vaccines employing this strategy have been tested in animals and humans (see, e.g., Bonese, et al., *Nature*, 252: 708-710 (1974); Killian, et al., *Pharmacol. Biochem. Behav.*, 9: 347-352 (1978); Carrera et al., *Nature*, 378: 727-730 (1995); Carrera et al., *Proc. Nat. Acad. Sci. USA*, 98: 1988-1992 (2001); Carrera et al., *Proc. Nat. Acad. Sci. USA*, 97: 6202-6206 (2000); Fox et al., *Nat. Med.*, 2: 1129-1132 (1996); Kantak et al., *Psychopharmacology* (Berl), 148: 251-262 (2000); and Moreno et al., *Mol. Pharm.*, 7: 431-441 (2010)). Although these approaches have had some success, they have been limited by the degree of immunity evoked by the addictive drug analog linked to the macromolecule carrier (see, e.g., Kantak et al., supra; Keyler et al., *Int. Immunopharmacol.*, 8: 1589-1594 (2008); and Kinsey et al., *Immunol. Cell Biol.*, 87: 309-314 (2009)).

Antibodies directed against certain addictive drugs have also been described (see, e.g., Hardin et al., *J. Pharmacol. Exp. Ther.*, 285: 1113-1122 (1998); Proksch et al., *J. Pharmacol. Exp. Ther.*, 292: 831-837 (2000); and Byrnes-Blake et al., *Int. Immunopharmacol.*, 1: 329-338 (2001)).

Thus, there is a need for alternative compositions and methods to prevent or treat drug addiction. This invention provides such compositions and methods. This and other advantages of the invention will become apparent from the detailed description provided herein.

BRIEF SUMMARY OF THE INVENTION

The invention provides a method of inducing an immune response against an antigen in a human. The method comprises administering to a human an adenovirus-antigen conjugate comprising (a) a disrupted adenovirus with a coat protein and (b) an antigen conjugated to the coat protein of the disrupted adenovirus, whereby the antigen is presented to the immune system of the human to induce an immune response against the antigen in the human.

The invention also provides an adenovirus-antigen conjugate comprising (a) a disrupted adenovirus with a coat protein and (b) an antigen conjugated to the coat protein of the disrupted adenovirus.

The invention provides a conjugate comprising (a) an isolated or purified adenovirus coat protein and (b) an antigen conjugated to the isolated or purified adenovirus coat protein.

The invention further provides an adeno-associated viral vector comprising a nucleic acid sequence which encodes an antibody directed against cocaine and which is operably linked to a promoter, wherein the nucleic acid sequence can be expressed in a human to produce the antibody.

DETAILED DESCRIPTION OF THE INVENTION

Figure 1:
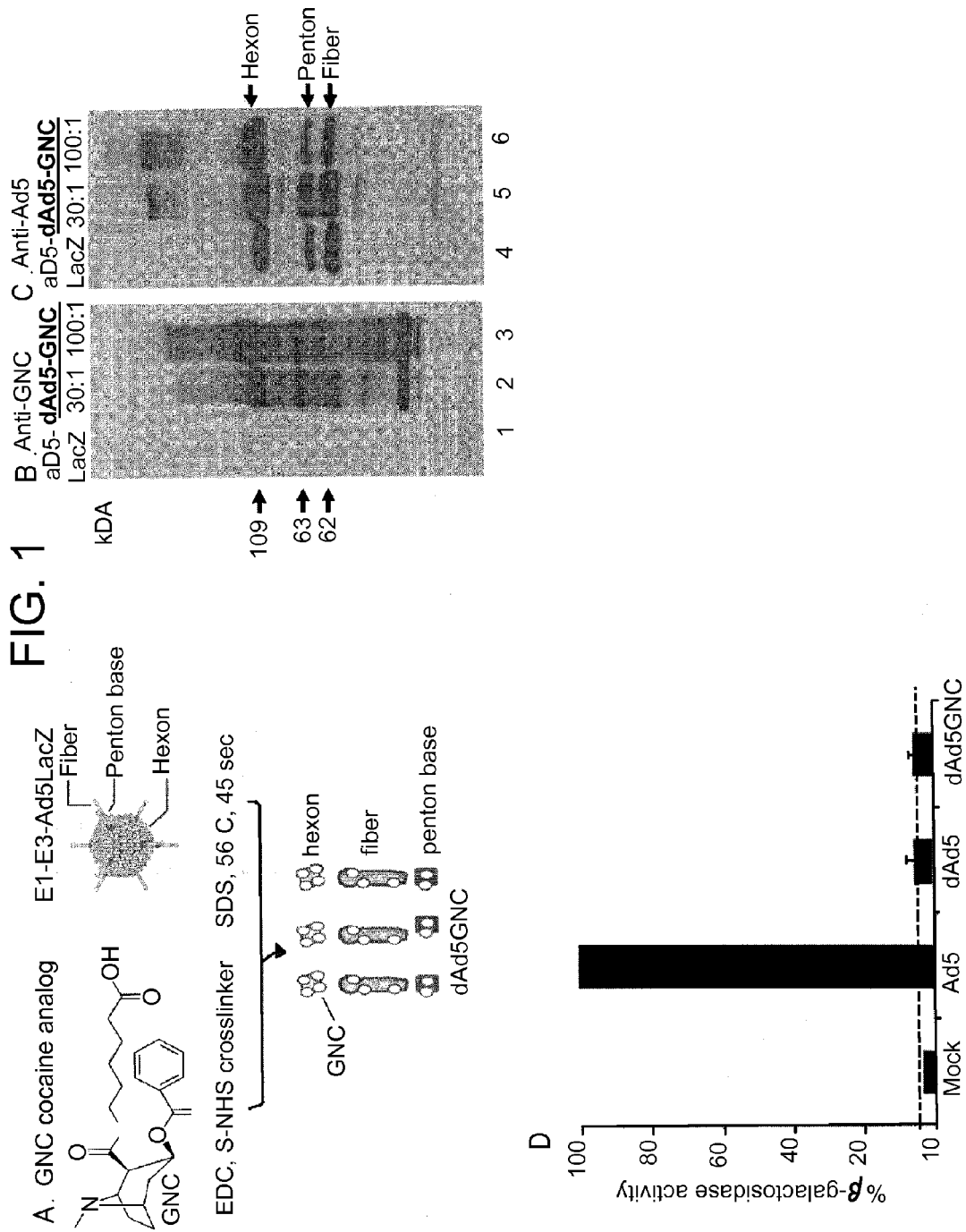
FIG. 1A is a diagram which illustrates the steps for conjugating GNC to adenovirus capsid proteins using 1-ethyl-3-[3-dimethylaminopropyl] carbodiimide hydrochloride (EDC) and N-hydroxysulfosuccinimide (S—NHS).
FIG. 1B is a Western blot showing that GNC is covalently coupled to the adenovirus capsid proteins (lane 1: Ad5LacZ, lane 2: GNC conjugated disrupted Ad5 (30:1), and lane 3: GNC conjugated disrupted Ad5 (100:1)).
FIG. 1C is a Western blot showing adenovirus capsid protein expression in an adenovirus-GNC conjugate (lane 4: unconjugated Ad5LacZ, lane 5: GNC conjugated disrupted Ad5 (30:1 ratio), and lane 6: GNC conjugated disrupted Ad5 (100:1)).
FIG. 1D is a graph which illustrates the lack of dAd5GNC infectious capacity assessed by the inability of the dAd5GNC vaccine to mediate expression of its LacZ transgene.

The invention is premised, at least in part, on the appreciation that an effective addictive drug vaccine can be generated by conjugating an antigen of an addictive drug, or derivative thereof, to the capsid of an adenovirus, particularly an adenovirus that has been disrupted (e.g., by treatment with heat and/or detergents). The reason that the adenovirus is an ideal carrier for the antigen of the addictive drug is that the adenovirus avidly interacts with antigen presenting cells (e.g., dendritic cells), and thus acts as an adjuvant to evoke immunity against itself. By coupling the antigen of the addictive drug to one or more of the adenovirus capsid proteins (e.g., hexon, penton base, fiber, protein IX, or other proteins), the immune system treats the antigen of the addictive drug as part of the adenovirus, and generates immunity against the drug.

While not wishing to be bound to any particular theory, it is believed that the addictive drug (or a derivative or analog thereof) becomes highly immunogenic because of the inherent properties of the adenovirus capsid, including its size and binding affinities (both endogenous as well as with genetically engineered enhanced binding affinities). Adenovirus (Ad) is a 36 kb double-stranded DNA virus that efficiently transfers DNA in vivo to a variety of different target cell types. The term "adenovirus," as used herein, includes "adenoviral vectors" as well as "adenoviral particles" or "adenovirus virions" propagated from adenoviral vectors. Thus, the terms "adenovirus," "adenoviral vectors," "adenoviral particles," and "adenovirus virions" are synonymous and can be used interchangeably. In the context of the inventive method, adenoviruses from various origins, subtypes, or mixture of subtypes can be used as the source of the viral genome for the adenoviral vector. While non-human adenovirus (e.g., simian, avian, canine, ovine, or bovine adenoviruses) can be used to generate the adenoviral vector, a human adenovirus preferably is used as the source of the viral genome for the adenoviral vector. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 (i.e., Ad1 through Ad51) are available from the American Type Culture Collection (ATCC, Manassas, Va.). Preferably, in the context of the invention, the adenovirus is of human subgroup C, especially serotype 2 or even more desirably serotype 5. However, non-group C adenoviruses can be used in the context of the invention. Preferred adenoviruses used in the construction of non-group C adenoviral vectors include Ad12 (group A), Ad7 and Ad35 (group B), Ad28 and Ad30 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and International Patent Application Publications WO 97/12986 and WO 98/53087.

The adenovirus can comprise a mixture of subtypes and thereby be a "chimeric" adenovirus. A chimeric adenovirus or adenoviral vector can comprise an adenoviral genome that is derived from two or more (e.g., 2, 3, 4, etc.) different adenovirus serotypes. In the context of the invention, a chimeric adenovirus or adenoviral vector can comprise approximately different or equal amounts of the genome of each of the two or more different adenovirus serotypes.

To circumvent pre-existing anti-adenovirus immunity in humans, adenoviral vectors based on novel adenovirus serotypes that are not human pathogens have been developed, including the C7 vector, which is based on a chimpanzee adenovirus (see, e.g., Farina et al., J. Virol., 75: 11603-11613 (2001), and Hashimoto et al., Infect. Immun., 73: 6885-6891 (2005)), as well as simian adenoviral vectors, including the sAd36 vector (see, e.g., Calcedo et al., J. Virol., 83: 2623-2631 (2009), and Roy et al., J. Gene Med., 13: 17-25 (2011)). Therefore, the adenovirus also can be based on a non-human primate adenovirus. For example, the adenovirus can be AdC7 or sAd36. Non-human primate serotypes do not circulate in the human population and, consequently, humans do not have pre-existing serum neutralizing antibodies. Even in the presence of pre-existing Ad5 immunity, vaccines based on non-human primate-derived serotypes are effective in generating potent humoral immune responses against relevant antigens conjugated thereto from a variety of pathogens.

The adenovirus of the invention is a disrupted adenovirus. A "disrupted" adenovirus is one that has been treated with heat and/or one or more detergents so as to render the adenovirus or adenoviral vector non-infectious in mammals, thereby improving their safety profile in vivo. In this respect, treating adenoviruses with a mild detergent has been shown to disrupt the viral capsid and to release the nucleoprotein core, groups of nine hexon capsomers, free peripentonal hexons, penton base, and fiber capsomers (see, e.g., Molinier-Frenkel et al., J. Virol., 76: 127-135 (2002), Boulanger et al., J. Gen. Virol., 44: 783-800 (1979), Boulanger, et al., FEBS Lett., 85: 52-56 (1978), and Nermut, The Architecture of Adenoviruses, pp. 5-34, in H. S. Ginsberg (ed.), "The Adenoviruses," Plenum Press, New York, N.Y. (1984)). Although disrupted adenovirus can be produced at high concentration, it is effective at relatively low doses even in the context of pre-existing anti-adenovirus immunity in humans for which intact, infectious adenovirus requires very large doses to overcome. The adenovirus can be treated with any suitable detergent known in the art that disrupts the structure of a virus. Examples of such detergents include sodium deoxycholate (DOC), sodium dodecyl sulfate (SDS). An adenovirus can be treated with "heat" by exposing the adenovirus to a temperature above about 50° C., e.g., about 50° C. to about 70° C. The adenovirus can be exposed to a temperature of about 50° C. or higher, about 55° C. or higher, about 60° C. or higher, or about 65° C. or higher. Alternatively, or in addition, the adenovirus can be exposed to a temperature of about 70° C. or lower, about 65° C. or lower, about 60° C. or lower, or about 55° C. or lower. Thus, the adenovirus can be exposed to a temperature between any two of the above endpoints. For example, the adenovirus can be exposed to a temperature of about 50° C. to about 55° C., about 55° C. to 60° C., about 60° C. to about 65° C., about 65° C. to about 70° C.

Preferably, the adenovirus or adenoviral vector is disrupted by treatment with heat and detergent prior to conjugation of an addictive drug (or analog thereof) to a coat protein of the adenovirus.

The adenovirus of the invention can be replication-competent. For example, the adenovirus can have a mutation (e.g., a deletion, an insertion, or a substitution) in the adenoviral genome that does not inhibit viral replication in host cells. The adenovirus also can be conditionally replication-competent. Preferably, however, the adenovirus desirably is replication-deficient in host cells.

By "replication-deficient" or "replication-defective" it is meant that the adenovirus requires complementation of one or more regions of the adenoviral genome that are required for replication, as a result of, for example, a deficiency in at least one replication-essential gene function (i.e., such that the adenoviral vector does not replicate in typical host cells, especially those in a human patient that could be infected by the adenovirus in the course of the inventive method). A deficiency in a gene, gene function, gene, or genomic region, as used herein, is defined as a mutation or deletion of sufficient genetic material of the viral genome to obliterate or impair the function of the gene (e.g., such that the function of the gene product is reduced by at least about 2-fold, 5-fold, 10-fold, 20-fold, 30-fold, or 50-fold) whose nucleic acid sequence was mutated or deleted in whole or in part. Deletion of an entire gene region often is not required for disruption of a replication-essential gene function. However, for the purpose of providing sufficient space in the adenoviral genome for one or more transgenes, removal of a majority of a gene region may be desirable. While deletion of genetic material is preferred, mutation of genetic material by addition or substitution also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA1 and/or VA-RNA-2).

The replication-deficient adenovirus or adenoviral vector desirably requires complementation of at least one replication-essential gene function of one or more regions of the adenoviral genome for viral replication. Preferably, the adenovirus requires complementation of at least one gene function of the E1A region, the E1B region, or the E4 region of the adenoviral genome required for viral replication (denoted an E1-deficient or E4-deficient adenoviral vector). Most preferably, the adenovirus is deficient in at least one replication-essential gene function (desirably all replication-essential gene functions) of the E1 region and at least one gene function of the nonessential E3 region (e.g., an Xba I deletion of the E3 region) (denoted an E1/E3-deficient adenoviral vector). With respect to the E1 region, the adenovirus can be deficient in part or all of the E1A region and/or part or all of the E1B region, e.g., in at least one replication-essential gene function of each of the E1A and E1B regions, thus requiring complementation of the E1A region and the E1B region of the adenoviral genome for replication. The adenovirus also can require complementation of the E4 region of the adenoviral genome for replication, such as through a deficiency in one or more replication-essential gene functions of the E4 region.

When the adenovirus is deficient in at least one replication-essential gene function in one region of the adenoviral genome (e.g., an E1- or E1/E3-deficient adenoviral vector), the adenovirus is referred to as "singly replication-deficient." A particularly preferred singly replication-deficient adenovirus is, for example, a replication-deficient adenovirus requiring, at most, complementation of the E1 region of the adenoviral genome, so as to propagate the adenovirus (e.g., to form adenovirus particles).

The adenovirus can be "multiply replication-deficient," meaning that the adenovirus is deficient in one or more replication-essential gene functions in each of two or more regions of the adenoviral genome, and requires complementation of those functions for replication. For example, the aforementioned E1-deficient or E1/E3-deficient adenovirus can be further deficient in at least one replication-essential gene function of the E4 region (denoted an E1/E4- or E1/E3/E4-deficient adenovirus or adenoviral vector), and/or the E2 region (denoted an E1/E2- or E1/E2/E3-deficient adenovirus or adenoviral vector), preferably the E2A region (denoted an E1/E2A- or E1/E2A/E3-deficient adenovirus or adenoviral vector).

Desirably, the adenovirus requires, at most, complementation of replication-essential gene functions of the E1, E2A, and/or E4 regions of the adenoviral genome for replication (i.e., propagation). However, the adenoviral genome can be modified to disrupt one or more replication-essential gene functions as desired by the practitioner, so long as the adenovirus remains deficient and can be propagated using, for example, complementing cells and/or exogenous DNA (e.g., helper adenovirus) encoding the disrupted replication-essential gene functions. In this respect, the adenovirus can be deficient in replication-essential gene functions of only the early regions of the adenoviral genome, only the late regions of the adenoviral genome, both the early and late regions of the adenoviral genome, or all adenoviral genes (i.e., a high capacity adenovector (HC-Ad), see Morsy et al., *Proc. Natl. Acad. Sci. USA*, 95: 965-976 (1998), Chen et al., *Proc. Natl. Acad. Sci USA*, 94: 1645-1650 (1997), and Kochanek et al., *Hum. Gene Ther.*, 10: 2451-2459 (1999)). Suitable replication-deficient adenoviruses or adenoviral vectors, including singly and multiply replication-deficient adenoviral vectors, are disclosed in U.S. Pat. Nos. 5,837,511, 5,851,806, 5,994,106, 6,127,175, 6,482,616, and 7,195,896; U.S. Patent Application Publications 2001/0043922 A1, 2002/0004040 A1, 2002/0110545 A1, and 2004/0161848 A1; and International Patent Application Publications WO 94/28152, WO 95/02697, WO 95/16772, WO 95/34671, WO 96/22378, WO 97/12986, WO 97/21826, and WO 03/022311.

In addition to modification (e.g., deletion, mutation, or replacement) of adenoviral sequences encoding replication-essential gene functions, the adenoviral genome can contain benign or non-lethal modifications, i.e., modifications which do not render the adenovirus replication-deficient, or, desirably, do not adversely affect viral functioning and/or production of viral proteins, even if such modifications are in regions of the adenoviral genome that otherwise contain replication-essential gene functions. Such modifications commonly result from DNA manipulation or serve to facilitate expression vector construction. For example, it can be advantageous to remove or introduce restriction enzyme sites in the adenoviral genome. Such benign mutations often have no detectable adverse effect on viral functioning.

Replication-deficient adenoviral vectors are typically produced in complementing cell lines that provide gene functions not present in the replication-deficient adenoviral vectors, but required for viral propagation, at appropriate levels in order to generate high titers of viral vector stock. Desirably, the complementing cell line comprises, integrated into the cellular genome, adenoviral nucleic acid sequences which encode gene functions required for adenoviral propagation. The cell line preferably is further characterized in that it contains the complementing genes in a non-overlapping fashion with the adenoviral vector, which minimizes, and practically eliminates, the possibility of the vector genome recombining with the cellular DNA. Construction of such a complementing cell lines involve standard molecular biology and cell culture techniques, such as those described by Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994).

Complementing cell lines for producing the adenovirus include, but are not limited to, 293 cells (described in, e.g., Graham et al., *J. Gen. Virol.*, 36, 59-72 (1977)), PER.C6 cells (described in, e.g., International Patent Application Publication WO 97/00326, and U.S. Pat. Nos. 5,994,128 and 6,033,908), and 293-ORF6 cells (described in, e.g., International Patent Application Publication WO 95/34671 and Brough et al., *J. Virol.*, 71: 9206-9213 (1997)). Additional complementing cells are described in, for example, U.S. Pat. Nos. 6,677,156 and 6,682,929, and International Patent Application Publication WO 03/20879. In some instances, the cellular genome need not comprise nucleic acid sequences, the gene products of which complement for all of the deficiencies of a replication-deficient adenovirus or adenoviral vector. One or more replication-essential gene functions lacking in a replication-deficient adenoviral vector can be supplied by a helper virus, e.g., an adenoviral vector that supplies in trans one or more essential gene functions required for replication of the desired adenoviral vector. Helper virus is often engineered to prevent packaging of infectious helper virus. For example, one or more replication-essential gene functions of the E1 region of the adenoviral genome are provided by the complementing cell, while one or more replication-essential gene functions of the E4 region of the adenoviral genome are provided by a helper virus.

The coat protein (e.g., hexon, fiber, and penton base) of an adenovirus can be manipulated to alter the recognition of the virus by the immune system of a particular host. For adenovirus, such manipulations can include deletion of regions of the fiber, penton, or hexon, insertions of various native or non-native ligands into portions of the coat protein, and the like. Manipulation of the coat protein can affect interactions of the adenovirus with antigen presenting cells in the host, thereby altering the immunogenicity of the adenovirus.

Any suitable technique for altering an adenovirus coat protein can be employed. For example, differing fiber lengths can be exploited. This optionally can be accomplished via the addition of a binding sequence to the penton base or fiber knob. This addition of a binding sequence can be done either directly or indirectly via a bispecific or multispecific binding sequence. In an alternative embodiment, the adenoviral fiber protein can be modified to reduce the number of amino acids in the fiber shaft, thereby creating a "short-shafted" fiber (as described in, for example, U.S. Pat. No. 5,962,311).

In yet another embodiment, the nucleic acid residues encoding amino acid residues associated with native structure of an adenovirus coat protein can be changed, supplemented, or deleted (see, e.g., International Patent Application Publication WO 00/15823, Einfeld et al., *J. Virol.*, 75(23): 11284-11291 (2001), and van Beusechem et al., *J. Virol.*, 76(6): 2753-2762 (2002)) such that the immunogenicity of an adenovirus incorporating the mutated nucleic acid residues (or having the fiber protein encoded thereby) in a mammal is altered (as compared to a wild-type adenovirus). In this respect, the native coxsackie virus and adenovirus receptor (CAR) and integrin binding sites of the adenovirus, such as the knob domain of the adenoviral fiber protein and an Arg-Gly-Asp (RGD) sequence located in the adenoviral penton base, respectively, can be removed or disrupted. Alternatively, amino acids can be added to the fiber knob as long as the fiber protein retains the ability to trimerize. Suitable residues include amino acids within the exposed loops of the serotype 5 fiber knob domain, such as, for example, the AB loop, the DE loop, the FG loop, and the HI loop, which are further described in, for example, Roelvink et al., *Science*, 286: 1568-1571 (1999), and U.S. Pat. No. 6,455,314. Any suitable amino acid residue(s) of a penton base protein can be mutated or removed. Suitable residues include, for example, one or more of the five RGD amino acid sequence motifs located in the hypervariable region of the Ad5 penton base protein (as described, for example, in U.S. Pat. No. 5,731,190).

In a preferred embodiment, the inventive method comprises an adenovirus with a coat protein and an antigen conjugated to the coat protein. The antigen can be conjugated to any coat protein, such as a hexon, a fiber, or a penton base. An "antigen" is a molecule that induces an immune response in a mammal against a pathogen or compound from which the antigen originates. An "immune response" can entail, for example, antibody production and/or the activation of immune effector cells (e.g., T cells). The antigen can comprise any epitope thereof, which ideally provokes an immune response in a mammal, especially a human, against the antigen. By "epitope" is meant a structure that is recognized by an antibody or an antigen receptor. Epitopes also are referred to in the art as "antigenic determinants."

An antigen in the context of the invention can comprise any subunit, fragment, or epitope of any proteinaceous molecule, including a protein or peptide of viral, bacterial, parasitic, fungal, protozoan, prion, cellular, or extracellular origin, which ideally provokes an immune response in mammal, preferably leading to protective immunity. The antigen also can be a small molecule. The term "small molecule" refers to a substance or compound having a molecular weight of less than about 1,000 g/mol. Desirably, the small molecule of the invention is a hapten. By "hapten" is meant a small molecule capable of eliciting an immune response only when conjugated to a carrier substance, such as a protein, which can be processed by antigen presenting cells and presented to the immune system. Typically, a hapten is a modified version of a small molecule which can be coupled to the carrier substance (e.g., an adenovirus capsid protein) and presented to the immune system of a host in such a way that the immune system recognizes the unmodified small molecule. Further, the hapten is characterized as the specificity-determining portion of the hapten-carrier conjugate, that is, it is capable of reacting with an antibody specific to the hapten in its free state. In a non-immunized addicted subject, there is an absence of formation of antibodies to the hapten.

A "pathogen" is an infectious agent that causes disease to its host. Suitable pathogens include, for example, viruses, bacteria, parasites, fungi (e.g., *Aspergillus*), protozoa, or prions. In one embodiment, the pathogen is a virus. The antigen can be a peptide isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae (e.g., Norovirus (also known as "Norwalk-like virus")), Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae (e.g., Hepatitis B virus or Hepatitis C virus), Herpesviridae (e.g., Human herpesvirus (HSV) 1, 2, 3, 4, 5, and 6, Cytomegalovirus, and Epstein-Barr Virus (EBV)), Hypoviridae, Iridoviridae, Leviviridae, Lipothrixviridae, Microviridae, Orthomyxoviridae (e.g., Influenzavirus A and B), Papovaviridae, Papillomaviridae (e.g., human papillomavirus (HPV)), Paramyxoviridae (e.g., measles, mumps, and human respiratory syncytial virus (RSV)), Parvoviridae, Picornaviridae (e.g., poliovirus, rhinovirus, hepatovirus, and aphthovirus (e.g., foot and mouth disease virus)), Poxviridae (e.g., vaccinia virus), Reoviridae (e.g., rotavirus), Retroviridae (e.g., lentivirus, such as human immunodeficiency virus (HIV) 1 and HIV 2), Rhabdoviridae, and Totiviridae. The antigenic peptides specifically recited herein are merely exemplary as any viral protein can be used in the context of the invention.

Alternatively or in addition, the antigen can be a peptide that is isolated from a bacterium. The peptide can originate from any bacterium including, but not limited to, *Actinomyces, Anabaena, Bacillus, Bacteroides, Bdellovibrio, Caulobacter, Chlamydia* (e.g., *Chlamydia trachomatis*), *Chlorobium, Chromatium, Clostridium* (e.g., botulinum toxin), *Corynebacterium diphtheria* (e.g., diphtheria toxin), *Cytophaga, Deinococcus, Escherichia, Halobacterium, Heliobacter, Hyphomicrobium, Methanobacterium, Micrococcus, Myobacterium* (e.g., *Mycobacterium tuberculosis*), *Mycoplasma, Myxococcus, Neisseria, Nitrobacter, Oscillatoria, Prochloron, Proteus, Pseudomonas, Phodospirillum, Rickettsia, Salmonella, Shigella* (e.g., Shigella toxin), *Spirillum, Spirochaeta, Staphylococcus, Streptococcus, Streptomyces, Sulfolobus, Thermoplasma, Thiobacillus*, and *Treponema*.

In another embodiment, the antigen can be a peptide isolated from a parasite such as, but not limited to, a parasite of the phylum Sporozoa (also referred to as phylum Apicomplexa), Ciliophora, Rhizopoda, or Zoomastigophora. The antigen also can be a toxin, or a portion thereof (peptide or non-peptide), produced by an animal. The toxin can be produced by any animal. Examples of such toxins include tetrodotoxin (produced by puffer fish), anatoxin-a (produced by algae), batrachotoxins (produced by amphibians), steroidal alkaloids (produced by amphibians), and snake venom.

Alternatively, the antigen can be isolated from a human, i.e., the antigen can be any constituent of a human's own tissues that is capable of stimulating autoimmunity (i.e., a "self antigen"). The antigen also can be a tumor antigen. By "tumor antigen" is meant an antigen that is expressed by tumor cells but not normal cells, or an antigen that is expressed in normal cells but is overexpressed in tumor cells. Examples of suitable tumor antigens include, but are not limited to, β-catenin, BCR-ABL fusion protein, K-ras, N-ras, PTPRK, NY-ESO-1/LAGE-2, SSX-2, TRP2-INT2, CEA, gp100, kallikrein 4, prostate specific antigen (PSA), TRP-1/gp75, TRP-2, tyrosinase, EphA3, HER-2/neu, MUC1, p53, mdm-2, PSMA, RAGE-1, surviving, telomerase, and WT1. Other tumor antigens are known in the art and are described in, for example, The Peptide Database of T-Cell Defined Tumor Antigens, maintained by the Ludwig Institute for Cancer Research; Van den Eynde et al., *Curr. Opin. Immunol.*, 9: 684-93 (1997); Houghton et al., *Curr. Opin. Immunol.*, 13: 134-140 (2001); and van der Bruggen et al., *Immunol. Rev.*, 188: 51-64 (2002). The antigen also can be a hormone or growth factor that is required for tumor growth (e.g., luteinizing hormone releasing hormone (LHRH)).

In another embodiment, the antigen is an antigen of an addictive drug. In this respect, the antigen can be a portion of the addictive drug (i.e., an epitope), an analog or derivative of the addictive drug, or a mimotope of an addictive drug, which induces an immune response against the addictive drug. By "mimotope" is meant a macromolecule, such as a peptide, which mimics the structure of an epitope and causes an antibody response identical to the one elicited by the epitope. By "analog" or "derivative" it is meant that the antigen has one or more different atoms, functional groups, or substructures in place of or in addition to native atoms, groups, or substructures.

By "portion" is meant an amino acid sequence that comprises at least three amino acids (e.g., about 3 to about 800 amino acids). Preferably, a "portion" comprises 3 or more (e.g., 5 or more, 10 or more, 15 or more, 20 or more, 25 or more, 30 or more, 40 or more, 50 or more, or 100 or more) amino acid residues, but less than the entire antigen (e.g., 800 or less, 700 or less, 600 or less, 500 or less, 400 or less, 300 or less, 200 or less, or 100 or less amino acid residues). Preferably, a portion is about 3 to about 500 amino acids (e.g., about 10, 100, 300, or 500 amino acids), about 3 to about 300 amino acids (e.g., about 20, 50, or 200 amino acids), or about 3 to about 100 amino acids (e.g., about 15, 40, 60, 70, or 90 amino acids), or a range defined by any two of the foregoing values. More preferably, a "portion" comprises no more than about 300 amino acids (e.g., about 3 to about 250 amino acids, about 10 to about 200 amino acids, or about 50 to about 100 amino acids, or a range defined by any two of the foregoing values).

The use of an analog, derivative, or portion of an addictive drug can offer several benefits in the invention, such as, for example, to facilitate conjugation to an adenoviral coat protein or to enhance the immune response. Desirably, the analog, derivative, or portion is capable of eliciting an immune response that is equal to or greater than the immune response generated by the addictive drug from which it is derived. For example, an adenovirus comprising an analog of an addictive drug may generate antibodies having a higher titer, specificity, affinity and/or avidity for the solution conformation of the addictive drug as compared to antibodies generated in response to an adenovirus comprising the drug from which the analog is derived.

The antigen can be any addictive drug, or portion or analog thereof. Exemplary classes of addictive drugs suitable for use in the invention include, without limitation, opioids, morphine derivatives, depressants, dissociative anesthetics, cannabinoids, hallucinogens, stimulants, prescription medications, anabolic steroids, inhalants, and club drugs. Specific examples of drugs within these classes include, without limitation, nicotine, cocaine, fentanyl, heroin, morphine, opium, oxycodone, hydrocodone, ketamine, PCP, barbiturates, benzodiazepines, flunitrazepam, GHB, methaqualone, hashish, marijuana, LSD, mescaline, psilocybin, amphetamine, cocaine, MDMA, methamphetamine, and methylphenidate.

In one embodiment, the antigen can be nicotine. Several nicotine haptens, carriers, and methods of conjugation have been described. Nicotine can be conjugated to an adenovirus using any suitable method known in the art. For example, nicotine can be conjugated to an adenoviral coat protein via a linker at the 6-position or at the 1-position as previously described for nicotine-BSA conjugates and nicotine-KLH conjugates (see, e.g., Matsushita et al., *Biochem. Biophys. Res. Comm.*, 57: 1006-1010 (1974); Castro et al., *Eur. J. Biochem.*, 104: 331-340 (1980); Noguchi et al., *Biochem. Biophys. Res. Comm.*, 83: 83-86 (1978); and Isomura et al., *J. Org. Chem.*, 66: 4115-4121 (2001)). Nicotine also can be conjugated to an adenovirus via the pyridine ring as described in International Patent Application Publication WO 99/61054, or the pyrrolidine ring as described in U.S. Pat. No. 6,232,082.

The antigen also can be an analog of nicotine. Suitable nicotine analogs include any nicotine analog that induces an immune response in a mammal (humoral or cell-mediated). Nicotine analogs are known in the art (see, e.g., Cerny et al., *Onkologie*, 25: 406-411 (2002); Lindblom et al., *Respiration*, 69: 254-260 (2002); de Villiers et al., *Respiration*, 69: 247-253 (2002); Tuncok et al., *Exp. Clin. Psychopharmacol.*, 9: 228-234 (2001); Hieda et al., *Int. J. Immunopharmacol.*, 22: 809-819 (2000); Pentel et al., *Pharmacol. Biochem. Behav.*, 65: 191-198 (2000); Isomura et al., *J. Org. Chem.*, 66: 4115-4121 (2001); and Meijler et al., *J. Am. Chem. Soc.*, 125: 7164-7165 (2003). For example, the nicotine analog can be N-succinyl-6-amino-(+/−)-nicotine (Castro et al., Biochem. *Biophys. Res. Commun.*, 67: 583-589 (1975)), 6-(sigma-aminocapramido)-(+/−)-nicotine (Noguchi et al., *Biochem. Biophys. Res. Comm.*, 83: 83-86 (1978)), O-succinyl-3'-hydroxymethyl-nicotine (Langone et al., *Biochemistry*, 12: 5025-5030 (1973); and *Meth. Enzymol.*, 84: 628-640 (1982)), or 3'-(hydroxymethyl)-nicotine hemisuccinate (Langone et al., supra, Abad et al., *Anal. Chem.*, 65: 3227-3231 (1993)). Additional examples of nicotine analogs suitable for use in the invention are described in U.S. Pat. Nos. 6,232,082 and 6,932,971. In a preferred embodiment, the nicotine analog is AM3. Novel nicotine analogs also can be used in the context of the invention, and examples of novel nicotine analogs are described in, e.g., International Patent Application Publication WO 2009/149252.

In another embodiment, the antigen can be cocaine. For example, the free acid of cocaine, diazonium salts of benzoyl cocaine and benzoyl ecognine, or the para-imino ester derivatives of cocaine and norcocaine (described in, e.g., U.S. Pat. Nos. 4,123,431; 4,197,237; and 6,932,971) can be conjugated to an adenovirus. A cocaine analog preferably is designed such that chemical coupling to the adenovirus proteins minimizes the formation of non-cocaine like structures, yet maintains the antigenic determinant of the cocaine moiety (see, e.g., Carrera et al., *Nature,* 378: 727-730 (1995)). Additional examples of cocaine analogs suitable for use as an antigen of the invention are described in U.S. Pat. No. 5,876,727. In addition, the antigen can be an acylated ecgonine methyl ester, a succinylated ecgonine methyl ester, a succinylated norcocaine, or benzoyl ecgonine. Preferably, the antigen is the cocaine analog 6-(2R,3S)-3-(benzoyloxy)-8-methyl-8-azabicyclo [3.2.1]octane-2-carbonyloxy-hexanoic acid (GNC) or 6-((2R,3S)-3-(benzoyloxy)-8-methyl-8-azabicyclo [3.2.1] octane-2-carboxamido) hexanoic acid) (GNE).

Methods of conjugating a hapten to a protein carrier are well known in the art, and can be readily adapted to the conjugation of an antigen to an adenoviral coat protein. Such methods are described in, e.g., Sambrook et al., supra, Ausubel, et al., supra, and Harlow and Lane, *Antibodies: A Laboratory Manual*, Cold Spring Harbor Laboratory, Cold Spring Harbor, N.Y. (1988).

There are a large number of functional groups which can be used to facilitate the conjugation of a hapten to an adenoviral coat protein. These include functional moieties such as carboxylic acids, anhydrides, mixed anhydrides, acyl halides, acyl azides, alkyl halides, N-maleimides, imino esters, isocyanates, amines, thiols, isothiocyanates, and others known in the art. These moieties are capable of forming a covalent bond with a reactive group of a an adenoviral coat protein. Depending upon the functional moiety used, the reactive group may be the free amino group of a lysine residue or a free thiol group of a cysteine residue on an adenoviral coat protein which, when reacted, results in amide, amine, thioether, amidine urea, or thiourea bond formation. One of ordinary skill in the art will recognize that other suitable activating groups and conjugation techniques can be used, such as those described in Wong, *Chemistry of Protein Conjugation and Cross-Linking* (CRC Press, Inc., 1991); Hermanson, *Bioconjugate Techniques* (Academic Press, 1996); and Dick and Beurret, "Conjugate Vaccines," *Contrib. Microbiol. Immunol.,* 10: 48-114 (Karger, Basal, 1989).

The antigen can be conjugated to an adenoviral coat protein using a homo-bifunctional cross-linker, such as glutaraldehyde, DSG, BM[PEO]4, or BS3, which has functional groups reactive towards amine groups or carboxyl groups of an adenoviral coat protein. Desirably, the antigen is conjugated to an adenoviral coat protein by way of chemical cross-linking using a hetero-bifunctional cross-linker. Generally, in the first step of the procedure (often referred to as derivatization) the adenovirus is reacted with the cross-linker, thereby resulting in an adenovirus containing one or more activated coat proteins. In the second step, unreacted cross-linker is removed using methods such as gel filtration or dialysis. In the third step, the antigen is reacted or "coupled" with the activated coat protein. In an optional fourth step, unreacted antigen is removed.

Several hetero-bifunctional cross-linkers are known in the art. For example, the hetero-bifunctional cross-linker can contain a functional group which reacts with the free amino group of lysine residues of an adenoviral coat protein, and a functional group which reacts with a cysteine residue or sulfhydryl group present on the antigen, thereby leading to the formation of a thioether linkage. The cysteine residue or sulfhydryl group can be naturally present on the antigen, made available for reaction by reduction, or engineered or attached on the antigen (e.g., a hapten) and optionally made available for reaction by reduction. Several such hetero-bifunctional cross-linkers are known in the art, and include, for example, SMPH, Sulfo-MBS, Sulfo-EMCS, Sulfo-GMBS, Sulfo-SIAB, Sulfo-SMPB, Sulfo-SMCC, SVSB, and SIA, which are commercially available from, for example, Pierce Thermo Fisher Scientific (Rockford, Ill., USA).

A preferred linker is a succinyl functional moiety, which forms succinimidyl ester cross-links of the antigen to epsilon amino groups exposed on an adenoviral capsid surface (Leopold et al., *Hum. Gene Ther.,* 9: 367-378 (1998) and Miyazawa et al., *J. Virol.,* 73: 6056-6065 (1999)). Examples of linkers comprising a succinyl functional moiety are N-hydroxysulfosuccinimide (Sulfo-NHS) and its uncharged analog N-hydroxysuccinimide (NHS), which are used to convert carboxyl groups to amine-reactive Sulfo-NHS esters. The presence of Sulfo-NHS esters increases the efficiency of coupling reactions mediated by carbodiimide compounds, such as EDAC (1-ethyl-3-[3-dimethylamino-propyl]carbodiimide hydrochloride), which couple carboxyl groups to primary amines and which also can be used in conjunction with Sulfo-NHS. Maleimides, which conjugate to sulfhydryl groups, can also be used to conjugate an antigen of an addictive drug to a coat protein of an adenovirus.

The amount of antigen that is conjugated per adenoviral particle is one factor which regulates the immune response induced by the antigen. Various strategies which are known in the art can be used in accordance with the invention to optimize the amount of conjugated antigen. For example, the extent of derivatization of the adenoviral coat protein with cross-linker can be influenced by varying experimental conditions such as the concentration of each of the reaction partners, the excess of one reagent over the other, the pH, the temperature, and the ionic strength. Similarly, the degree of coupling, i.e., the amount of antigen per adenoviral particle, can be adjusted by varying the experimental conditions described above to match the requirements of the vaccine. The degree of coupling can also be expressed as the amount of antigen per adenoviral capsomere. By "capsomere" is meant a morphological subunit of the adenovirus capsid formed from the major coat proteins. The outer capsid of an adenoviral virion consists of 252 capsomeres (see, e.g., van Oostrum and Burnett, *J. Virol.,* 56: 439-448 (1985)). The ratio of adenoviral capsomere to antigen molecule (i.e., Ad:Ag) utilized to prepare the inventive adenovirus-antigen conjugates can be, for example, 1:1 or more, e.g., 1:3 or more, 1:10 or more, or 1:30 or more. Alternatively, or in addition, the Ad:Ag ratio can be 1:1000 or less, e.g., 1:500 or less, 1:300 or less, or 1:100 or less. Thus, the Ad:Ag ratio can be bounded by any two of the above endpoints. For example, the Ad:Ag ratio can be 1:-1:1000, 1:3-1:500, 1:10-1:300, 1:10-:100, or 1:30-:100.

Once the adenoviral capsid proteins have been conjugated to an antigen, the relative extent of conjugation can be determined qualitatively by Western blotting for the hapten and quantitatively by mass spectrometry (e.g., MALD-TOF MS) or by measuring free functional groups on the adenovirus coat protein by colorimetric assay. Achieving a conjugation rate of 0.3 to 2.0 antigen molecules per capsomere (or approximately 80 to 500 antigen molecules per adenoviral particle) would be comparable to the conjugation levels observed for the fluorophore, Cy3, as previously described (Leopold et al., *Hum. Gene Ther.,* 9: 367-378 (1998)). An "overconjugated" adenovirus can be beneficial for hapten-mediated vaccination. Therefore, the number of antigen molecules per adenoviral particle in an overconjugated adenovirus can be 40 or more, e.g., 80 or more, 120 or more, or 200 or more. Alternatively, or in addition, the number of antigen molecules per adenoviral particle in an overconjugated adenovirus can be 1000 or less, e.g., 750 or less, 500 or less, or 300 or less. Thus, the number of antigen molecules per adenoviral particle can be bounded by any two of the above endpoints. For example, the number of antigen molecules per adenoviral particle in an overconjugated adenovirus can be 40-1000, 80-750, 120-500, 200-500, or 200-300.

Assuming equal affinity for antigen, there may be a direct correlation between antibody titer and vaccine efficacy. Therefore, increasing the amount of antigen that is conjugated to the adenovirus may enhance the immunogenicity thereof. Exposed lysine residues on an adenoviral capsid protein (e.g., hexon) provide a free amine group that is a target for conjugation to carboxylate group-containing antigens, and many of the aforementioned cross-linking reagents react preferentially with lysine residues.

It may be advantageous to add or to remove one or more lysine residues to the adenoviral coat protein in order to maximize the attachment of antigen molecules to the adenovirus coat protein. Thus, the adenovirus coat protein desirably comprises one or more non-native lysine residues (e.g., 1 or more, 3 or more, 5 or more, or 7 or more lysine residues). Alternatively, or in addition, the number of non-native lysine residues can be 25 or less, e.g., 20 or less, 15 or less, or 10 or less. Thus, the number of non-native lysine residues can be bounded by any two of the above endpoints. For example, the number of non-native lysine residues can be 1-25, 3-20, 5-10, 5-15, or 7-10.

The coat protein that comprises at least one non-native lysine residue or lacks at least one native lysine residue can be any adenovirus coat protein (e.g., fiber, penton base, or hexon). Preferably, the coat protein that comprises at least one non-native lysine or in which at least one native lysine residue is absent is a hexon protein. When non-native lysine residues are added to a hexon protein, it is preferred that the lysine residues are incorporated into one or more flexible loops of the hexon protein. Standard molecular biology techniques which are well known in the art can be utilized to generate modified coat proteins in accordance with the invention (see, e.g., Sambrook et al., supra, and Ausubel, et al., supra).

In another embodiment of the invention, the adenovirus can comprise one or more transgenes, each encoding a protein that stimulates one or more cells of the immune system. By "transgene" is meant any heterologous nucleic acid sequence that can be carried by an adenoviral vector and expressed in a cell. A "heterologous nucleic acid sequence" is any nucleic acid sequence that is not obtained from, derived from, or based upon a naturally occurring nucleic acid sequence of the adenovirus. The adenovirus can comprise at least one transgene as described herein, i.e., the adenovirus can comprise one transgene as described herein or more than one transgene as described herein (i.e., two or more of transgenes). The transgene preferably encodes a protein (i.e., one or more nucleic acid sequences encoding one or more proteins). An ordinarily skilled artisan will appreciate that any type of nucleic acid sequence (e.g., DNA, RNA, and cDNA) that can be inserted into an adenovirus can be used in connection with the invention.

In a preferred embodiment, the transgene encodes a protein that enhances the immune response in an animal. For example, the transgene can encode a protein that elevates the humoral immune response to haptens on the adenovirus capsid. Alternatively, the transgene can encode a protein that enhances the cell-mediated immune response to the adenovirus-antigen conjugate. The one or more transgenes can encode, for example, a dendritic cell activating protein (e.g., CD40L), a B cell activating protein (e.g., B-cell Activating Factor (BAFF)), a T cell activating protein (e.g., IL-15), or combinations thereof. Preferably, the one or more transgenes encode a protein that stimulates B cell activity. Most preferably, the adenovirus comprises a transgene encoding BAFF.

The one or more transgenes in the adenovirus desirably are present as part of an expression cassette, i.e., a particular nucleotide sequence that possesses functions which facilitate subcloning and recovery of a nucleic acid sequence (e.g., one or more restriction sites) or expression of a nucleic acid sequence (e.g., polyadenylation or splice sites). The one or more transgenes can be located in any suitable region of the adenovirus. Preferably, the one or more transgenes are located in the E1 region (e.g., replaces the E1 region in whole or in part). For example, the E1 region can be replaced by one or more expression cassettes comprising a transgene. Additionally or alternatively, the one or more transgenes can be located in the E4 region (e.g., replaces the E4 region in whole or in part).

Preferably, the transgene is operably linked to (i.e., under the transcriptional control of) one or more promoter elements. Techniques for operably linking sequences together are well known in the art. A "promoter" is a DNA sequence that directs the binding of RNA polymerase and thereby promotes RNA synthesis. A nucleic acid sequence is "operably linked" to a promoter when the promoter is capable of directing transcription of the nucleic acid sequence. A promoter can be native or non-native to the nucleic acid sequence to which it is operably linked.

Any promoter (i.e., whether isolated from nature or produced by recombinant DNA or synthetic techniques) can be used in connection with the invention to provide for transcription of a heterologous nucleic acid sequence (e.g., a transgene). The promoter preferably is capable of directing transcription in a eukaryotic (desirably mammalian) cell. Any suitable promoter sequence can be used in the context of the invention. In this respect, the transgene can be operably linked to a viral promoter. Suitable viral promoters include, for instance, cytomegalovirus (CMV) promoters (described in, for example, U.S. Pat. Nos. 5,168,062 and 5,385,839, and GenBank accession number X17403), promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the herpes thymidine kinase promoter (Wagner et al., Proc. Natl. Acad. Sci., 78: 144-145 (1981)), promoters derived from SV40 or Epstein Barr virus, and the like.

Alternatively, the transgene can be operably linked to a cellular promoter, i.e., a promoter that drives expression of a cellular protein. Preferred cellular promoters for use in the invention will depend on the desired expression profile of the transgene. In one aspect, the cellular promoter is preferably a constitutive promoter that works in a variety of cell types, such as cells of the immune system (e.g., dendritic cells). Suitable constitutive promoters can drive expression of genes encoding transcription factors, housekeeping genes, or structural genes common to eukaryotic cells. Constitutively active cellular promoters are known in the art and include, for example, the Ying Yang 1 (YY1) promoter, the JEM-1 promoter, the ubiquitin promoter, and the elongation factor alpha (EF1α) promoter.

Instead of being a constitutive promoter, the promoter can be an inducible promoter, i.e., a promoter that is up- and/or down-regulated in response to an appropriate signal. A promoter can be up-regulated by a radiant energy source or by a substance that distresses cells. For example, a promoter can be up-regulated by drugs, hormones, ultrasound, light activated compounds, radiofrequency, chemotherapy, and cryofreezing. Thus, the promoter sequence that regulates expression of the transgene sequence can contain at least one heterologous regulatory sequence responsive to regulation by an exogenous agent. Suitable inducible promoter systems include, but are not limited to, the IL-8 promoter, the metallothionine inducible promoter system, the bacterial lacZYA expression system, the tetracycline expression system, and the T7 polymerase system. Further, promoters that are selectively activated at different developmental stages (e.g., globin genes are differentially transcribed from globin-associated promoters in embryos and adults) can be employed. In another embodiment, the promoter can be a tissue-specific promoter, i.e., a promoter that is preferentially activated in a given tissue and results in expression of a gene product in the tissue where activated. A tissue-specific promoter suitable for use in the invention can be chosen by the ordinarily skilled artisan based upon the target tissue or cell-type.

Operable linkage of a transgene to a promoter is within the skill of the art, and can be accomplished using routine recombinant DNA techniques, such as those described in, for example, Sambrook et al., supra, and Ausubel et al., supra.

To optimize protein production, preferably the transgene further comprises a polyadenylation site 3' of the coding sequence of the transgene. Any suitable polyadenylation sequence can be used, including a synthetic optimized sequence, as well as the polyadenylation sequence of BGH (Bovine Growth Hormone), mouse globin D (MGD), polyoma virus, TK (Thymidine Kinase), EBV (Epstein Barr Virus), and the papillomaviruses, including human papillomaviruses and BPV (Bovine Papilloma Virus). A preferred polyadenylation sequence is the SV40 (Human Sarcoma Virus-40) polyadenylation sequence. Also, preferably all the proper transcription signals (and translation signals, where appropriate) are correctly arranged such that the each nucleic acid sequence is properly expressed in the cells into which it is introduced. If desired, the heterologous nucleic acid sequence also can incorporate splice sites (i.e., splice acceptor and splice donor sites) to facilitate mRNA production.

The invention also provides adeno-associated viral (AAV) vector comprising a nucleic acid sequence which encodes an antibody directed against cocaine and which is operably linked to a promoter, wherein the nucleic acid sequence can be expressed in a human to produce the antibody. AAV is a DNA virus, which is not known to cause human disease. AAV requires co-infection with a helper virus (i.e., an adenovirus or a herpes virus), or expression of helper genes, for efficient replication. Delivering the AAV rep protein enables integration of the AAV vector comprising AAV ITRs into a specific region of genome, if desired. Host cells comprising an integrated AAV genome show no change in cell growth or morphology (see, for example, U.S. Pat. No. 4,797,368). The nucleic acid sequence which encodes an antibody directed against cocaine can encode any such antibody (or portion thereof) known in the art. For example, the nucleic acid sequence can encode the cocaine-binding monoclonal antibody GNC92H2 (Redwan et al., *Biotechnol. Bioeng.*, 82(5): 612-8 (2003)). In another embodiment, a nucleic acid sequence encoding an antibody which has been isolated from a mammal vaccinated with the conjugate of the invention can be used. Independent of the source of the antibody against cocaine, the nucleic acid sequence encoding an antibody can encode a whole antibody molecule, or any antigen-binding fragment thereof, such as Fab, Fab', F(ab')2, single-chain Fvs (scFv), single-chain antibodies, disulfide-linked Fvs, or fragments comprising either a $V_L$ or $V_H$ domain. Moreover, the nucleic acid sequence desirably encodes a monoclonal antibody.

An antibody produced in a mammal in response to the administration of the inventive adenovirus-antigen conjugate, the inventive conjugate comprising an adenovirus coat protein and an antigen, or the inventive adeno-associated viral vector can be isolated and used for a variety of purposes. When the antibody is isolated from a non-human mammal, the antibody can be humanized for subsequent administration to a human. "Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, framework region residues of the human immunoglobulin are replaced by corresponding non-human residues. Furthermore, humanized antibodies can comprise residues which are not found in the recipient antibody or in the donor antibody. These modifications are made to further refine antibody performance. A humanized antibody can comprise substantially all of at least one and, in some cases two, variable domains, in which all or substantially all of the hypervariable regions correspond to those of a non-human immunoglobulin and all, or substantially all, of the framework regions are those of a human immunoglobulin sequence. The humanized antibody optionally also will comprise at least a portion of an immunoglobulin constant region, typically that of a human immunoglobulin. For further details, see Jones et al., *Nature*, 321: 522-525 (1986), Reichmann et al., *Nature*, 332: 323-329 (1988), and Presta, *Curr. Op. Struct. Biol.*, 2: 593-596 (1992). Methods of preparing humanized antibodies are generally well known in the art and can readily be applied to the antibodies produced by the methods described herein.

The invention also provides an adenovirus-antigen conjugate comprising an adenovirus with a coat protein and an antigen of an addictive drug conjugated to the coat protein of the adenovirus. Descriptions of the adenovirus, addictive drug antigen, conjugation, etc., set forth above in connection with embodiments of the inventive methods also are applicable to those same aspects of the aforesaid adenovirus-antigen conjugate.

The invention further provides a conjugate comprising an isolated or purified adenovirus coat protein and an antigen conjugated to the isolated or purified adenovirus coat protein. By "isolated" is meant the removal of a nucleic acid or protein from its natural environment. By "purified" is meant that a given nucleic acid or protein, whether one that has been removed from nature (including genomic DNA and mRNA) or synthesized (including cDNA) and/or amplified under laboratory conditions, has been increased in purity, wherein "purity" is a relative term, not "absolute purity." It is to be understood, however, that nucleic acids and proteins may be formulated with diluents or adjuvants and still for practical purposes be isolated. For example, nucleic acids will be mixed with an acceptable carrier or diluent when used for introduction into cells.

The coat protein can be any adenovirus coat protein described herein, such as a hexon protein, a fiber protein, or a penton base protein. Descriptions of the antigen, conjugation, etc., set forth above in connection with embodiments of the inventive methods and inventive adenovirus-antigen conjugate also are applicable to those same aspects of the aforesaid conjugate comprising an isolated or purified adenovirus coat protein. As discussed above, an antigen can be conjugated to an adenovirus coat protein via lysine residues. When an antigen is conjugated to an adenoviral coat protein via lysine residues, it may be advantageous to add or to remove one or more lysine residues to the adenoviral coat protein in order to maximize the attachment of antigen molecules to the adenovirus coat protein. Thus, the isolated or purified adenovirus coat protein desirably comprises one or more non-native lysine residues (e.g., 1 or more, 3 or more, 5 or more, or 7 or more lysine residues). Alternatively, or in addition, the number of non-native lysine residues can be 25 or less, e.g., 20 or less, 15 or less, or 10 or less. Thus, the number of non-native lysine residues can be bounded by any two of the above endpoints. For example, the number of non-native lysine residues can be 1-25, 3-20, 5-10, 5-15, or 7-10.

The invention provides compositions comprising (a) the adenovirus-antigen conjugate and (b) a carrier therefor. The invention also provides a composition comprising (a) the conjugate comprising the isolated or purified adenovirus coat protein and the antigen, and (b) a carrier therefore. Preferably, the composition is a pharmaceutically acceptable (e.g., physiologically acceptable) composition, which comprises a carrier, preferably a pharmaceutically (e.g., physiologically acceptable) carrier and the adenovirus-antigen conjugate. Any suitable carrier can be used within the context of the invention, and such carriers are well known in the art. The choice of carrier will be determined, in part, by the particular site to which the composition is to be administered and the particular method used to administer the composition. The composition preferably is free of replication-competent adenovirus. The composition optionally can be sterile with the exception of the adenovirus-antigen conjugate described herein.

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the conjugate is administered in a composition formulated to protect the conjugate from damage prior to administration. For example, the composition can be formulated to reduce loss of the conjugate on devices used to prepare, store, or administer the conjugate, such as glassware, syringes, or needles. The composition can be formulated to decrease the light sensitivity and/or temperature sensitivity of the conjugate. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the conjugate, facilitate administration, and increase the efficiency of the inventive method. Formulations for adenovirus-containing compositions are further described in, for example, U.S. Pat. No. 6,225,289, U.S. Pat. No. 6,514,943, U.S. Patent Application Publication 2003/0153065 A1, and International Patent Application Publication WO 00/34444.

A composition also can be formulated to enhance transduction efficiency. In addition, one of ordinary skill in the art will appreciate that the conjugate can be present in a composition with other therapeutic or biologically-active agents. For example, factors that control inflammation, such as ibuprofen or steroids, can be part of the composition to reduce swelling and inflammation associated with in vivo administration of the conjugate. Immune system stimulators or adjuvants, e.g., interleukins, lipopolysaccharide, and double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

The conjugate preferably is administered to a mammal (e.g., a human), whereupon an immune response against the antigen is induced. The immune response can be a humoral immune response, a cell-mediated immune response, or, desirably, a combination of humoral and cell-mediated immunity. Ideally, the immune response provides a clinical benefit upon exposure to the antigen. When the antigen is an addictive drug, or analog thereof, a "clinical benefit" can be, for example, a reduction in the physiological effects of the addictive drug, a reduction in the reward or pleasure associated with use of the addictive drug, or a reduction in the likelihood of regaining an addiction to the drug. However, a clinical benefit is not required in the context of the invention. The inventive method further can be used for antibody production and harvesting. For example, the inventive method can be used to produce antibodies for diagnostic purposes (e.g., to detect the presence of an addictive drug or antigen in the blood).

Administering the conjugate can be one component of a multistep regimen for inducing an immune response in a mammal. In particular, the inventive method can represent one arm of a prime and boost immunization regimen. In this respect, the method further comprises administering to the mammal a boosting composition after administering the composition comprising the inventive conjugate to the mammal. In this embodiment, therefore, the immune response is "primed" upon administration of the composition containing the inventive adenovirus-antigen conjugate, and is "boosted" upon administration of the boosting composition. Alternatively, the inventive method further comprises administering to the mammal a priming composition to the mammal prior to administering the composition comprising the inventive adenovirus-antigen conjugate to the mammal. In this embodiment, therefore, the immune response is "primed" upon administration of the priming composition, and is "boosted" upon administration of the composition containing the adenovirus-antigen conjugate.

The priming composition or the boosting composition can comprise the inventive conjugate (e.g., the inventive adenovirus-antigen conjugate), or a gene transfer vector that comprises a nucleic acid sequence encoding the antigen of interest (or analog thereof). Any gene transfer vector can be employed, including viral and non-viral gene transfer vectors. Examples of suitable viral gene transfer vectors include, but are not limited to, retroviral vectors, adeno-associated virus vectors, vaccinia virus vectors, herpesvirus vectors, parainfluenza-RSV chimeric vectors (PIV-RSV), and adenoviral vectors. Examples of suitable non-viral vectors include, but are not limited to, plasmids, liposomes, and molecular conjugates (e.g., transferrin). Preferably, the priming composition or the boosting composition comprises a plasmid or an adenoviral vector. Alternatively, an immune response can be primed or boosted by administration of an antigen itself (or an analog thereof) with or without a suitable adjuvant.

In one embodiment, both the priming composition and boosting composition comprises an adenovirus-antigen conjugate that employs a serotype 5 adenovirus (Ad5). Alternatively, the priming composition and the boosting composition each comprise an adenovirus of a different serotype. For example, the priming composition can comprise a adenovirus-antigen conjugate that employs a serotype 5 adenovirus, while the boosting composition can comprise an adenovirus-antigen conjugate that employs a non-human primate adenovirus (e.g., C7 or sAd36). Conversely, the priming composition can comprise an adenovirus-antigen conjugate that employs a non-human primate adenovirus (e.g., C7 or sAd36), while the boosting composition can comprise a adenovirus-antigen conjugate that employs a serotype 5 adenovirus. One of ordinary skill in the art will appreciate that any combination of adenovirus serotypes can be used in a prime-boost regimen so as to maximize the immune response elicited against a particular antigen.

In another embodiment, both the priming composition and the boosting compositions comprise the inventive conjugate comprising the isolated or purified adenovirus coat protein and the antigen. In this respect, the conjugate of the priming composition and the boosting composition can comprise the same or different adenovirus coat protein, which can be derived from the same or different adenovirus serotype. For example, the priming composition can include a conjugate comprising a hexon protein from a human (e.g., Ad5) or non-human primate (e.g., C7 or sAd36) adenovirus, while the boosting composition can include a conjugate comprising an hexon protein from the same or different adenovirus. Alternatively, the priming composition can include a conjugate comprising a fiber protein from a human (e.g., Ad5) or non-human primate (e.g., C7 or sAd36) adenovirus, while the boosting composition can include a conjugate comprising a hexon protein from a human (e.g., Ad5) or non-human primate (e.g., C7 or sAd36) adenovirus.

In yet another embodiment, the priming composition can comprise an adenovirus-antigen conjugate, while the boosting composition can comprise a conjugate comprising an adenovirus coat protein and an antigen. Alternatively, the priming composition can comprise a conjugate comprising an adenovirus coat protein and an antigen, while the boosting composition can comprise an adenovirus-antigen conjugate.

Administration of the priming composition and the boosting composition can be separated by any suitable timeframe, e.g., 1 week or more, 2 weeks or more, 4 weeks or more, 8 weeks or more, 12 weeks or more, 16 weeks or more, 24 weeks or more, 52 weeks or more, or a range defined by any two of the foregoing values. The boosting composition preferably is administered to a mammal (e.g., a human) 2 weeks or more (e.g., 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 20 weeks, 24 weeks, 28 weeks, 35 weeks, 40 weeks, 50 weeks, 52 weeks, or a range defined by any two of the foregoing values) following administration of the priming composition. More than one dose of priming composition and/or boosting composition can be provided in any suitable timeframe. The dose of the priming composition and boosting composition administered to the mammal depends on a number of factors, including the extent of any side-effects, the particular route of administration, and the like.

Any route of administration can be used to deliver the conjugate to the mammal. Indeed, although more than one route can be used to administer the conjugate, a particular route can provide a more immediate and more effective reaction than another route. Preferably, the conjugate is administered via intramuscular injection. A dose of conjugate also can be applied or instilled into body cavities, absorbed through the skin (e.g., via a transdermal patch), inhaled, ingested, topically applied to tissue, or administered parenterally via, for instance, intravenous, peritoneal, or intraarterial administration.

The conjugate can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the conjugate. The conjugate also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of conjugate administered to the mammal will depend on a number of factors, including the size of a target tissue, the extent of any side-effects, the particular route of administration, and the like. The dose ideally comprises an "effective amount" of conjugate, i.e., a dose of conjugate which provokes a desired immune response in the mammal or production of the desired quantity of antibodies in the mammal. The desired immune response can entail production of antibodies, protection upon subsequent challenge, immune tolerance, immune cell activation, and the like. Similarly, the desired quantity of antibodies can provide protection upon subsequent challenge, immune tolerance, and the like.

With respect to the adenovirus-antigen conjugate, a single protein dose of adenovirus-antigen conjugate desirably is equivalent to about $1 \times 10^5$ or more particles (which also are referred to as particle units (pu)) of the adenovirus-antigen conjugate, e.g., about $1 \times 10^6$ or more particles, about $1 \times 10^7$ or more particles, about $1 \times 10^8$ or more particles, about $1 \times 10^9$ or more particles, or about $1 \times 10^{10}$ or more particles of the adenovirus-antigen conjugate. Alternatively, or in addition, a single protein dose of adenovirus-antigen conjugate is equivalent to about $1 \times 10^{14}$ particles or less of the adenovirus-antigen conjugate, e.g., about $1 \times 10^{13}$ particles or less, about $1 \times 10^{12}$ particles or less, about $1 \times 10^{11}$ particles or less, about $1 \times 10^{10}$ particles or less, or about $1 \times 10^9$ particles or less of the adenovirus-antigen conjugate. Thus, a single protein dose of adenovirus-antigen conjugate can comprise a quantity of protein of the adenovirus-antigen conjugate in a range defined by any two of the aforementioned values. For example, a single protein dose of adenovirus-antigen conjugate can be equivalent to $1 \times 10^5$-$1 \times 10^{14}$ particles, $1 \times 10^6$-$1 \times 10^{12}$ particles, $1 \times 10^8$-$1 \times 10^{11}$ particles, $1 \times 10^9$-$1 \times 10^{12}$ particles, $1 \times 10^9$-$1 \times 10^{11}$ particles, $1 \times 10^9$-$1 \times 10^{10}$ particles, or $1 \times 10^{10}$-$1 \times 10^{12}$ particles, of the adenovirus-antigen conjugate. In other words, a single protein dose of adenovirus-antigen conjugate can be equivalent to, for example, about 1×10$^6$ pu, 2×10$^6$ pu, 4×10$^6$ pu, 1×10$^7$ pu, 2×10$^7$ pu, 4×10$^7$ pu, 1×10$^8$ pu, 2×10$^8$ pu, 4×10$^8$ pu, 1×10$^9$ pu, 2×10$^9$ pu, 4×10$^9$ pu, 1×10$^{10}$ pu, 2×10$^{10}$ pu, 4×10$^{10}$ pu, 1×10$^{11}$ pu, 2×10$^{11}$ pu, 4×10$^{11}$ pu, 1×10$^{12}$ pu, 2×10$^{12}$ pu, or 4×10$^{12}$ pu of the adenovirus-antigen conjugate.

The conjugate can be administered in conjunction with counseling and/or one or more additional agents that prevent or treat drug addiction. The additional agent may treat withdrawal symptoms, facilitate quitting, or prevent relapse. When the adenovirus is conjugated to a nicotine hapten, the additional agent can be, for example, an anti-depressant, a nicotine receptor modulator, a cannabinoid receptor antagonist, an opioid receptor antagonist, a monoamine oxidase inhibitor, an anxiolytic, or any combination of these agents. Preferably, the additional agent is an anti-depressant selected from the group consisting of bupropion, doxepin, desipramine, clomipramine, imipramine, nortriptyline, amitriptyline, protriptyline, trimipramine, fluoxetine, fluvoxamine, paroxetine, sertraline, phenelzine, tranylcypromine, amoxapine, maprotiline, trazodone, venlafaxine, mirtazapine, and pharmaceutically active salts or optical isomers thereof. When the adenovirus is conjugated to a cocaine hapten, the additional agent can be, for example, an opioid receptor antagonist, an anti-depressant such as desipramine or fluoxetine, or an agent which regulates the dopaminergic system (e.g., bromocriptine or buprenorphine).

The following examples further illustrate the invention but should not be construed as in any way limiting its scope.

EXAMPLE 1

This example demonstrates a method of inducing an immune response against cocaine in a mammal using an adenovirus conjugated to a cocaine analog.

An adenovirus-cocaine conjugate (dAd5GNC) was generated by covalently conjugating the cocaine analog GNC (6-(2R,3S)-3-(benzoyloxy)-8-methyl-8-azabicyclo [3.2.1] octane-2-carbonyloxy-hexanoic acid) to a disrupted serotype 5 E1/E3-deficient adenoviral vector. Specifically, an E1/E3-deficient serotype 5 adenoviral vector (Ad5) comprising a LacZ gene inserted into the deleted E1 region was disrupted by treatment with sodium dodecyl sulfate (SDS) at 56° C. for 45 seconds, followed by the covalent linking of GNC to the Ad5 capsid proteins with 1-ethyl-3-[3-dimethylaminopropyl] carbodiimide hydrochloride (EDC) and N-hydroxysulfosuccinimide (S—NHS) (FIG. 1A).

Western analysis of the conjugate comprising the cocaine analog and the disrupted adenovirus at two ratios of GNC to Ad capsomere (i.e., 30:1 and 100:1) indicated that the GNC content was greater at the 100:1 ratio (FIG. 1B). Increasing the GNC analog to Ad capsomere ratio showed no further increase in conjugation levels. The anti-adenovirus immunity induced by the conjugate was robust, and was independent of the ratio of GNC to Ad capsomeres (FIG. 1C). Based on this data, the dAd5GNC conjugate with the GNC to Ad capsomere ratio of 100:1 was selected for subsequent experiments.

To demonstrate that the dAd5GNC vaccine was not infectious, the ability of the conjugate to express the LacZ transgene in A549 cells was assessed. In this respect, A549 cells were exposed to Ad5LacZ (Ad5), disrupted Ad5LacZ (dAd5), or dAd5LacZ-GNC (dAd5GNC) (at a GNC:Ad capsomere ratio of 100:1). β-galactosidase activity in cell lysates resulting from the expression of the LacZ transgene was assessed 48 hours after exposure to Ad5, dAd5, or dAd5GNC. Whereas the non-conjugated, non-disrupted E1/E3-deficient Ad5LacZ vector (Ad5) was capable of mediating expression of the LacZ transgene, neither the non-conjugated disrupted Ad5LacZ vector (dAd5) nor the dAd5LacZ-GNC conjugate (dAd5GNC) were capable of mediating β-galactosidase expression (FIG. 1D).

BALB/c mice (n=20) were vaccinated intramuscularly with 4 μg dAd5GNC at 0, 3, and 6 weeks. Three weeks after the third immunization, Balb/c mice (n=4) were challenged with intravenous (IV) administration of $^3$H-cocaine (2.5 μg). After 1 minute, serum was obtained, mixed with protein G SEPHAROSE™, and assessed for bound $^3$H-cocaine (i.e., IgG bound) relative to the $^3$H-cocaine in the supernatant. Antibody titers were assessed by ELISA against BSA conjugated-GNC at 0, 2, 7, and 13 weeks. Anti-GNC ELISA titers were elicited with mean reciprocal titers of 7.2× 10$^5$±1.8×10$^5$ by 13 weeks (FIG. 2A).

Quantification of the time course of isotype-specific titers revealed an initial anti-GNC IgM specific titer that fell below detection levels by 5 weeks. Anti-GNC IgG1, IgG2a, and IgG2b titers were detectable at 2 weeks and steadily increased, with titers of IgG1 antibody greater than titers of IgG2a and IgG2b antibodies (FIG. 2B). A competitive ELISA assay demonstrated that the elicited antibodies recognized a moiety common to both cocaine and GNC with equal specificity (FIG. 2C). At 7 weeks after the third immunization, the $K_d$ for cocaine was 45±16 nM.

Figure 2:
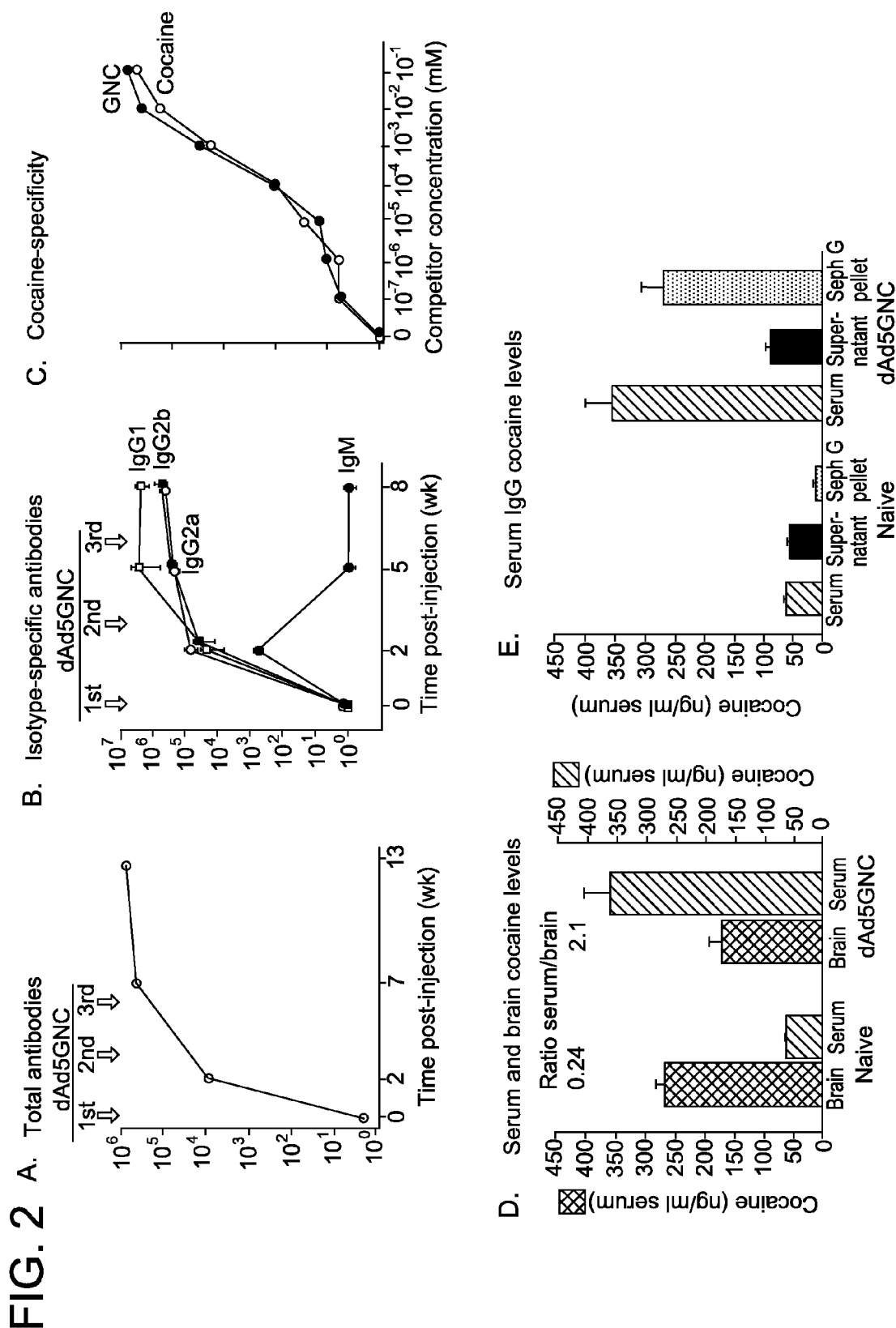
FIG. 2A is a graph which illustrates the total anti-GNC IgG antibody titers elicited over time as described in Example 1. BALB/c mice (n=20) were vaccinated intramuscularly with 4 µg dAd5GNC at 0, 3, and 6 weeks. Antibody titers were assessed by ELISA against BSA conjugated-GNC at 0, 2, 7, and 13 weeks, and are shown as mean values ±SEM.
FIG. 2B is a graph which illustrates the immunoglobulin isotypes of anti-GNC antibodies elicited by the methods described in Example 1. Serum was evaluated by ELISA using isotype-specific secondary antibodies for IgG1, IgG2a, IgG2b, and IgM. Antibody titers are shown as mean values ±SEM.
FIG. 2C is a graph which illustrates the inhibition of binding of dAd5GNC immune sera to BSA-GNC by ELISA in the presence of increasing concentrations of GNC or cocaine.
FIG. 2D is a graph which illustrates the levels of cocaine in the brain and serum of BALB/c mice challenged with $^3$H-cocaine in naïve and dAd5GNC-vaccinated mice. The figure shows cocaine levels in the brain (ng/g brain) and serum (ng/mL serum) of naïve and immunized mice, as well as the ratio of cocaine in blood to cocaine in brain (g/mL) in the treatment group.
FIG. 2E is a graph which illustrates the fraction of serum cocaine bound to IgG in Balb/c mice challenged with $^3$H-cocaine (2.5 µg). After exposure to $^3$H-cocaine for 1 minute, serum was obtained, mixed with protein G SEPHAROSE™, and assessed for bound $^3$H-cocaine (i.e., IgG bound) relative to the $^3$H-cocaine in the supernatant.

When $^3$H-cocaine was administered intravenously to the dAd5GNC mice, the levels of cocaine in the brain of immunized mice was reduced by 41% compared to naïve mice (FIG. 2D). Concurrently, the $^3$H-cocaine levels in the serum was increased by more than 5-fold, such that there was a 8.8-fold change in the ratio of blood to brain cocaine levels in the immunized mice. Serum collected at 1 minute post-injection and incubated with protein G SEPHAROSE™, demonstrated that 76% of the $^3$H-cocaine in serum was associated with an IgG antibody in the vaccinated mice (FIG. 2E).

Figure 3:
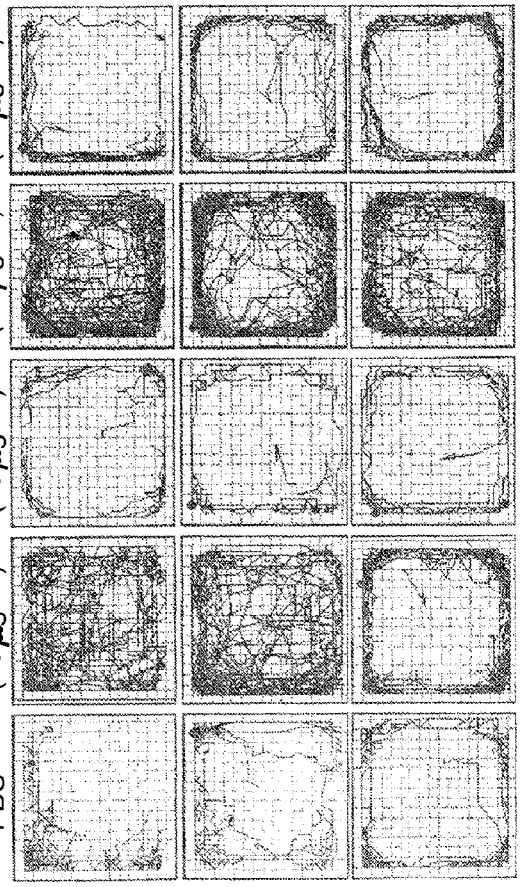
FIG. 3A is a schematic of visual tracings of the locomotor activity of naïve mice challenged with PBS (column 1), naïve mice challenged with 25 µg cocaine (column 2), dAd5GNC-vaccinated mice challenged with 25 µg cocaine (column 3), naïve mice challenged with 50 µg cocaine (column 4), and dAd5GNC-vaccinated mice challenged with 50 µg cocaine (column 4).
FIG. 3B is a graph which illustrates the cumulative ambulatory time of naïve and dAd5GNC-vaccinated mice as a function of time after challenge with PBS or 50 µg cocaine. The statistics (Kolmogorov-Smirnov test) for the treatment groups are as follows: (1) dAd5GNC+PBS (control) versus naïve+PBS (control) (D=0.18, p>0.14), (2) naïve+cocaine versus both controls, dAd5GNC+PBS (D=0.8, p<0.0001), and naïve+PBS (D=0.9, p<0.0001), (3) naïve+cocaine versus dAd5GNC+cocaine (D=0.7, p<0.0001), (4) dAd5GNC+cocaine versus both controls, naïve+PBS (D=0.35, p<0.0005), and dAd5GNC+PBS (D=0.21, p<0.0005).
FIG. 3C includes pie charts which illustrate the percent of time spent in ambulatory, vertical, stereotypic activity, and rest by naïve or dAd5GNC-vaccinated mice challenged with PBS or 50 µg cocaine. The statistics (Chi-square test) for the treatment groups are as follows: (1) dAd5GNC+PBS (control) versus naïve+PBS (control) ($X^2$=0.53, p>0.9), (2) naïve+cocaine versus both controls, dAd5GNC+PBS ($X^2$=28.0, p<0.0001) and naïve+PBS (p<0.0001), (3) naïve+cocaine versus dAd5GNC+cocaine, ($X^2$=32.5, p<0.0001), and (4) dAd5GNC+cocaine versus both controls, naïve+PBS ($X^2$=0.99, p>0.8), and dAd5GNC+PBS ($X^2$=1.6, p>0.6). All of the studies were carried out in a 27 cm×27 cm Med Associates chamber (St. Albans, Vt.).
Figure 3:
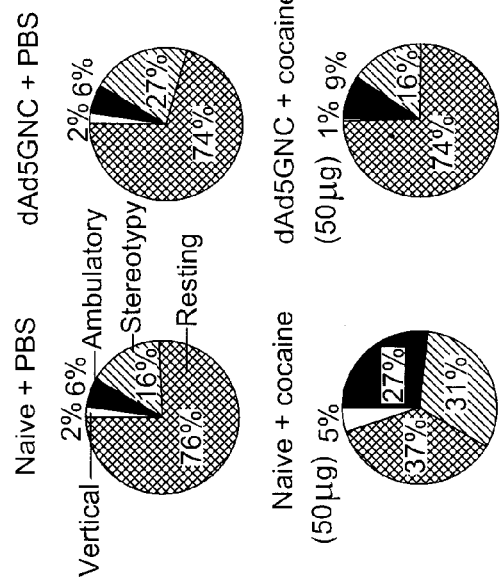
Figure 3:
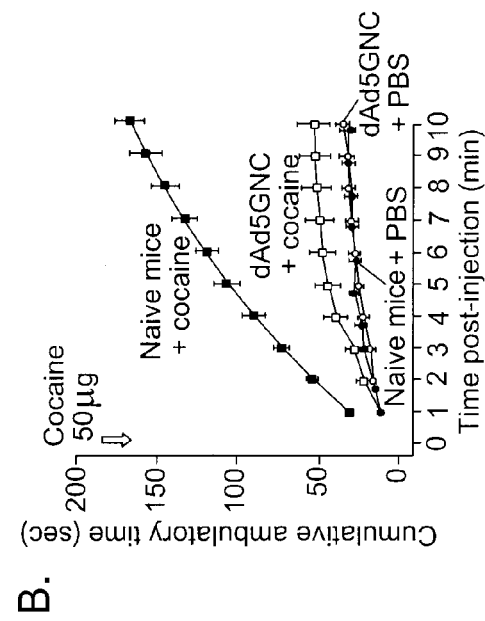

To demonstrate that the high anti-cocaine titers elicited by dAd5GNC could prevent cocaine administered at levels comparable to human doses from inducing hyperlocomotion in mice, vaccinated or naïve mice (n=15 per group) were challenged intravenously with cocaine (25 or 50 μg) or PBS, and locomotor activity was assessed in an open field apparatus. Naïve mice receiving intravenous injection of 25 or 50 μg of cocaine locomoted over more distance than did naïve mice receiving PBS (FIG. 3A). In contrast, dAd5GNC-vaccinated mice exposed to the same levels of cocaine exhibited activity similar to mice that were challenged with PBS. Quantitative measurement of the cumulative distance traveled plotted on a per minute basis demonstrated that naïve mice exhibited marked cocaine-induced ambulatory activity (FIG. 3B). While the dAd5GNC-vaccinated mice challenged with 50 μg cocaine displayed statistically greater ambulatory activity than the naïve PBS control (D=0.35; p<0.0005), the mice exhibited far less locomotor activity than naïve mice exposed to 50 μg cocaine (D=0.7; p<0.0001). Comparison of cumulative distance traveled showed the same results (p<0.0001). The relative time each mouse spent in ambulatory, stereotypic, vertical, and resting time was measured in naïve and vaccinated mice with and without the highest level cocaine challenge (50 μg). The distribution of these behaviors showed marked differences between naïve and immunized mice exposed to cocaine. Naïve and dAd5GNC-vaccinated mice challenged with PBS and the vaccinated mice challenged with cocaine showed behavioral phenotypes, all of which were distinct from cocaine-challenged naïve mice (FIG. 3C).

Figure 4:
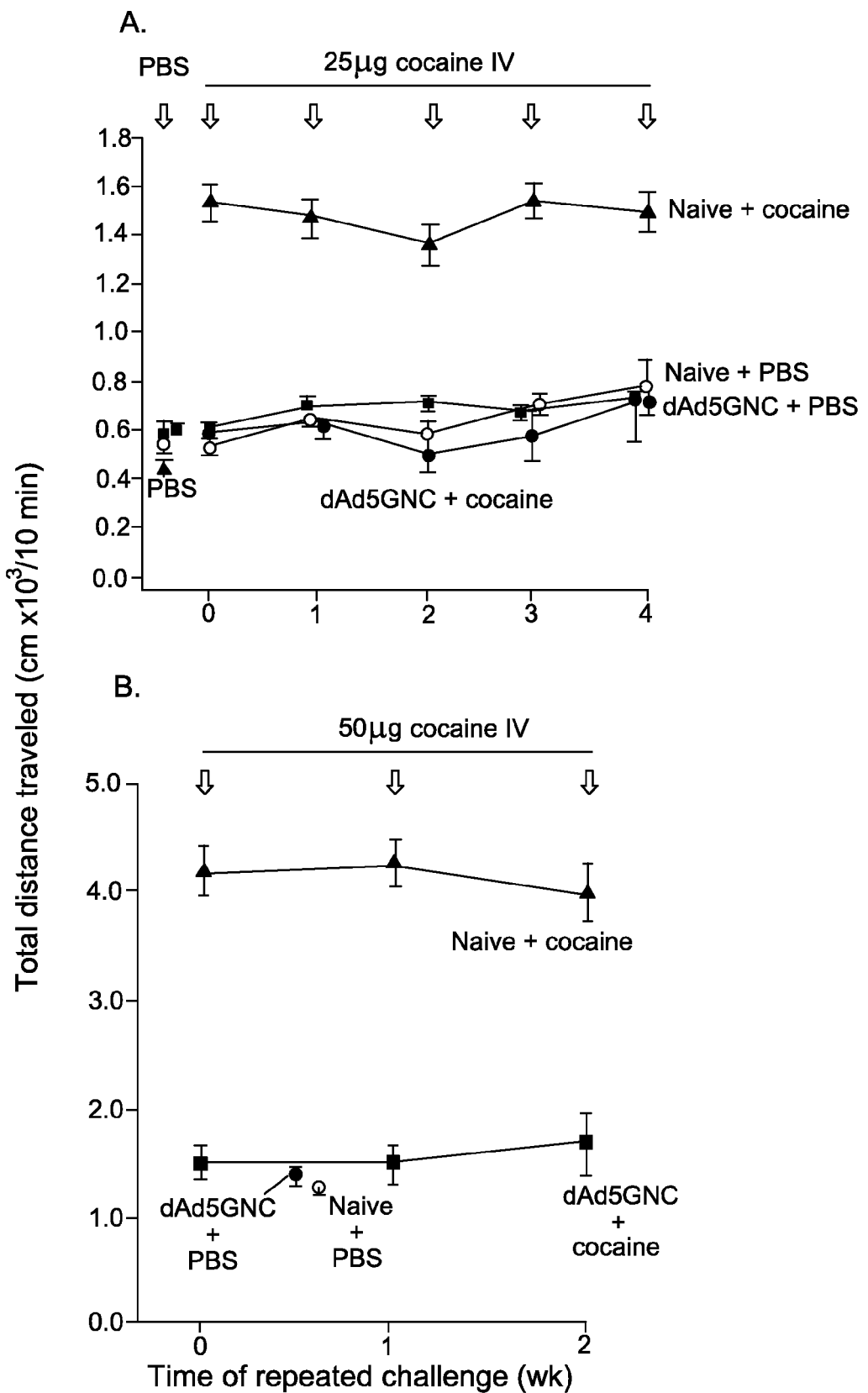
FIG. 4A is a graph which illustrates the total distance traveled by naïve and dAd5GNC-immunized Balb/c mice in 10 minutes immediately following cocaine (25 µg) or PBS challenge plotted for each sequential weekly trial (n=15/group). The statistics (repeated measures ANOVA) for the treatment groups are as follows: (1) dAd5GNC+cocaine versus naïve+cocaine (F=40.9, p<0.0005), (2) dAd5GNC+cocaine versus dAd5GNC+PBS (F=0.83, p>0.3), (3) dAd5GNC+cocaine versus naïve+PBS (F=0.1, p>0.7), and (4) dAd5GNC+PBS versus naïve+cocaine (F=190, p<0.0001); naïve+cocaine versus naïve+PBS (F=158, p<0.0001). All statistics by repeated measures ANOVA within groups had no significant difference among the repetitions (F=0.97, p>0.4).
FIG. 4B is a graph which illustrates the total distance traveled by naïve and dAd5GNC-immunized Balb/c mice in 10 minutes immediately following cocaine (50 µg) or PBS challenge plotted for each sequential weekly trial (n=15/group). The statistics (repeated measures ANOVA) for the treatment groups are as follows: (1) dAd5GNC+cocaine versus naïve+cocaine (F=14.4, p<0.006), (2) dAd5GNC+cocaine versus dAd5GNC+PBS (F=0.8, p>0.4), (3) dAd5GNC+cocaine versus naïve+PBS (F=1.3, p>0.2), (4) dAd5GNC+PBS versus naïve+cocaine (F=37.4, p<0.0001), and (5) naïve+cocaine versus naïve+PBS (F=46.2, p<0.0001). All statistics by repeated measures ANOVA within groups had no significant difference among the repetitions (F=0.08, p>0.9).

In successive weekly cocaine challenges, locomotor activity of the vaccinated mice was indistinguishable from naïve or vaccinated mice that received PBS challenge, and significantly less than naïve mice that received a cocaine challenge (FIGS. 4A and 4B). In each of the successive weekly cocaine challenges (at both the 25 µg and 50 µg doses), locomotor activity in vaccinated mice was the same as that for naïve or vaccinated mice that received PBS challenge, and was significantly different than naïve mice receiving a cocaine challenge. This was true for all other parameters assessed, including vertical, stereotypic, and resting time.

The results of this example demonstrate that an adenovirus conjugated to a cocaine analog can be utilized to induce an immune response against cocaine in a mammal.

EXAMPLE 2

This example demonstrates a method of inducing an immune response against cocaine in a mouse using an adenovirus conjugated to a cocaine analog.

A heat-disrupted (56° C. for 45 seconds in 0.5% SDS) serotype 5 E1/E3-deficient adenoviral vector was generated using methods known in the art and disclosed herein. The cocaine analog GNC (6-(2R,3S)-3-(benzoyloxy)-8-methyl-8-azabicyclo[3.2.1]octane-2-carbonyloxy hexanoic acid) was covalently linked to the adenoviral vector with the reagent 1-ethyl-3-[3-dimethylaminopropyl]carbodiimide HCl at Ad capsomere to GNC conjugation ratios of 1:30 or 1:100 to produce dAdGNC30 and dAdGNC100 conjugates, respectively.

Anti-GNC Western analysis showed effective conjugation of GNC to the hexon, penton, and fiber capsid proteins. BALB/c mice were immunized intramuscularly (IM) with the conjugates of dAdGNC30 and dAdGNC100 separately ($2 \times 10^{10}$ particle units) formulated in complete Freund's adjuvant, and subsequently boosted at three weeks with the same dose of immunogen in incomplete Freund's adjuvant. Serum anti-cocaine antibody titers were monitored by ELISA. At five weeks, dAdGNC30 elicited anti-cocaine antibody levels of $2.4 \times 10^5 \pm 4 \times 10^4$, while dAdGNC100 elicited anti-cocaine antibody levels of $1 \times 10^6 \pm 3 \times 10^5$. A competitive ELISA assay showed that the anti-cocaine antibodies reacted with high specificity to the cocaine moiety, and not to the short linker between the cocaine and adenovirus capsid proteins.

Anti-cocaine antibody isotype analysis by a specific ELISA assay showed that the levels of IgG2b were the highest, followed by IgG1 and IgG2a. To assess the efficacy of the anti-cocaine antibody evoked by the AdGNC100 at five weeks, the mice were challenged intravenously (IV) with $^3$H-cocaine (1.5 µg). After 1 minute, brain and serum levels of cocaine were quantified. The level of cocaine in the brains of dAdGNC100-immunized mice was reduced by 41% (p<0.01) compared to similarly challenged control naïve mice. Assessment of serum demonstrated that cocaine was sequestered in the blood, with a 4-fold increase in serum cocaine levels in the dAdGNC100 immunized mice.

The results of this example demonstrate that an adenovirus conjugated to a cocaine analog can induce a robust cocaine-specific humoral immune response in vivo and inhibit brain cocaine pharmacokinetics.

EXAMPLE 3

This example demonstrates that an adenovirus-antigen conjugate comprising a disrupted serotype 5 adenovirus circumvents pre-existing immunity to Ad5 in mice.

4 µg of a disrupted E1/E3-deleted Ad5 vector (dAd5GNC-produced as described above) or $2 \times 10^{10}$ pu of an intact (i.e., non-disrupted) E1/E3-deleted Ad5 vector (Ad5GNC) were coupled to GNC as described above and injected intramuscularly to naïve Balb/c mice (n=5) or mice having Ad5 antibodies (n=5). Mice were boosted at 3 weeks post prime. Total anti-GNC IgG antibody titers were assessed by ELISA against BSA conjugated-GNC at 0, 2, 3, 5 and 6 weeks post prime. At 6 weeks post prime, mice immunized with dAd5GNC had anti-GNC IgG antibody titers that were significantly higher than those receiving Ad5GNC (p<0.02). Ad5 preimmune mice that were immunized with intact Ad5GNC had significantly lower anti-GNC antibody titers than naïve mice receiving the same immunization (p<0.0006), whereas mice immunized with dAd5GNC had higher antibody titers, which were the same in preimmune or naïve mice (p>0.3)

Vaccinated or naive mice (n=15 per group) were challenged intravenously with cocaine (25 µg) or PBS and distance traveled in 10 minutes was assessed in an open field apparatus. dAd5GNC suppressed to baseline the cocaine induced hyperactivity in immunized mice. Ad5GNC immunization suppressed nearly 50% of the cocaine induced hyperactivity.

Cocaine levels in the brain (ng/g brain) and serum (ng/ml serum) of naïve and immunized mice were measured at one minute following 1.5 µg $^3$H-cocaine challenge in n=4 mice/group 5 weeks after the third immunization. Mice immunized with dAd5GNC sequestered 7-fold more cocaine in the blood than the naïve control. Mice immunized with intact Ad5GNC sequestered 5-fold more cocaine in the blood than the naïve control. Comparisons between groups were conducted by one-way paired two sample t-test.

The results of this example demonstrate that a disrupted adenovirus based on serotype 5 can evade pre-existing immunity to serotype 5 adenovirus. The results of this example also demonstrate that a conjugate comprising a disrupted Ad5 virus and a cocaine analog completely suppresses cocaine induced hyperactivity in mice, whereas a non-disrupted Ad5 virus suppresses cocaine-induced hyperactivity in mice by only 50%.

EXAMPLE 4

This example demonstrates a method of inducing an immune response against cocaine in a rat using an adenovirus conjugated to a cocaine analog.

A heat-disrupted (56° C. for 45 seconds in 0.5% SDS) serotype 5 E1/E3-deficient adenoviral vector was generated using methods known in the art and disclosed herein. The cocaine analog GNE 6-((2R,3S)-3-(benzoyloxy)-8-methyl-8-azabicyclo [3.2.1] octane-2-carboxamido)hexanoic acid) was covalently linked to the adenoviral vector with the reagent 1-ethyl-3-[3-dimethylaminopropyl]carbodiimide HCl to produce dAd5GNE.

Wistar rats (n=8) were immunized intramuscularly (IM) with 10 µg dAd5GNE, and subsequently boosted at three and five weeks with the same dose of dAd5GNE. Serum anti-cocaine antibody titers were monitored by ELISA. At five weeks, dAd5GNE elicited anti-cocaine antibody titers on the order of $10^6$.

To assess the efficacy of the anti-cocaine antibody evoked by the dAd5GNE, rats (n=4) were challenged intravenously (IV) with $^3$H-cocaine (3.0 µCi). After two minutes, rats were sacrificed and brain and serum levels of cocaine were quantified. Assessment of serum demonstrated that cocaine was sequestered in the blood, with a greater than 6-fold increase in serum cocaine levels in the dAd5GNE immunized rats as compared to naïve rats.

To demonstrate that the high anti-cocaine titers elicited by dAd5GNE could prevent cocaine administered at levels comparable to human doses from inducing hyperlocomotion in rats, vaccinated or naïve rats were challenged intravenously with cocaine (15 mg/kg) or PBS, and locomotor activity was assessed in an open field apparatus.

The relative time each rat spent in ambulatory, stereotypic, vertical, and resting time was measured in naïve and vaccinated rats with and without cocaine challenge. The distribution of these behaviors showed marked differences between naïve and immunized rats exposed to cocaine. Naïve and dAd5GNE-vaccinated rats challenged with PBS and the vaccinated rats challenged with cocaine showed behavioral phenotypes, all of which were distinct from cocaine-challenged naïve rats. Naïve rats receiving intravenous injection of 15 mg/kg of cocaine locomoted over more distance than did naïve rats receiving PBS. At 18 weeks, the distance traveled by dAd5GNE-vaccinated rats was reduced by 64% as compared to naïve rats challenged with cocaine ($p<0.0012$). The protection against cocaine was sustained, with a 56% reduction in the distance traveled by the dAd5GNE-vaccinated rats versus naïve rats challenged with cocaine at 25 days ($p<0.0018$).

Using assays to monitor cocaine self-administration, extinction, and reinstatement of responding for cocaine that are described in, e.g., International Patent Application Publication WO2009/149252, dAd5GNE was shown to block cocaine reward and drug seeking in vaccinated rats.

The results of this example demonstrate that a disrupted adenovirus conjugated to a cocaine analog can induce a high antibody titer sufficient to suppress cocaine-induced hyperactivity in vivo, and sequesters cocaine in the blood.

EXAMPLE 5

This example describes the generation of a conjugate comprising an isolated or purified adenovirus coat protein and an antigen of an addictive drug.

Figure 5:
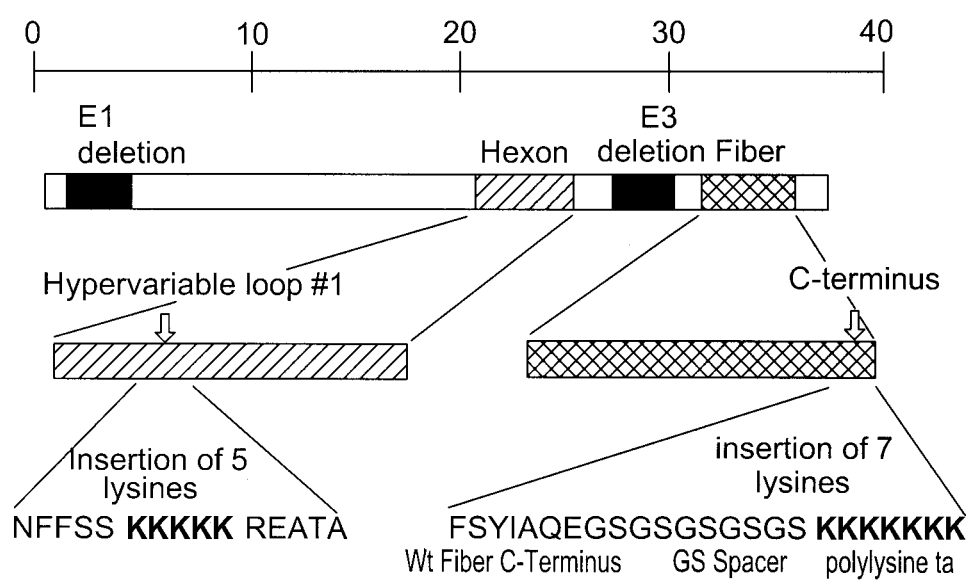
FIG. 5 is a diagram depicting the generation of adenovirus hexon and fiber proteins containing non-native lysine residues.

A recombinant serotype 5 (Ad5) E1, E3-deleted adenoviral vector containing a LacZ gene inserted into the deleted E1 region is propagated by serial expansion on 293 cells and purified by cesium chloride density gradient centrifugation (see, e.g., Rosenfeld et al., *Cell*, 68: 143-155 (1992)). Hexon and fiber proteins are purified from adenovirus that has been disrupted with urea by ion exchange chromatography (see, e.g., Maizel et al., *Virology*, 36: 126-136 (1968)). To make larger amounts of hexon and fiber, the pET *E. coli* expression system (Novagen/EMD Chemicals, Gibbstown, N.J.) with a cleavable histidine tag for affinity purification will be used. The amount of adenoviral vector and protein is quantified by the bicinchoninic acid assay (Pierce Protein Research Products, Rockford, Ill.). Hexon and fiber cDNA constructs will be derived from the plasmids used for adenovirus production. Adenoviral vectors containing wild-type hexon and fiber constructs, as well as adenoviral vectors containing lysine-modified capsid proteins in the hypervariable region of the hexon and C-terminus of fiber have been generated (see FIG. 5).

Coat proteins will be purified using standard chromatographic methods including affinity columns and commercially available antibody reagents. Conjugation of recombinant proteins will be performed in different capsid protein to GNE hapten ratios. After hexon- and fiber-GNE conjugate purification, complexes will be cross-linked to form multimers using maleimide crosslinkers via cysteine side chain sulfhydryls, followed by dialysis.

The synthesis of 6-((2R,3S)-3-(benzoyloxy)-8-methyl-8-azabicyclo [3.2.1] octane-2-carboxamido)hexanoic acid (GNE) is carried out by treatment of commercially available cocaine hydrochloride under acidic conditions resulting in the double ester hydrolysis yielding an ecgonine core with the correct stereochemistry. Coupling of a benzyl ester linker onto the carboxylic acid followed by benzoylation of the secondary alcohol yields the desired protected hapten. Ester deprotection under a hydrogen atmosphere yields GNE with the appropriate free acid moiety required for conjugation to the adenovirus coat proteins with amide linkages that impart chemical stability.

For conjugation of GNE to adenovirus coat proteins, GNE (0.3 mg) is activated overnight at 4° C. after the addition of 7.2 µl charging solution, which is made by dissolving 2.4 mg of 1-ethyl-3-[3-dimethylaminopropyl] carbodiimide hydrochloride and 2 mg of N-hydroxysulfosuccinimide in 4 µl $H_2O$ and 40 µl dimethylformamide. Disruption of the Ad5 vector described above is carried out at 56° C. for 45 seconds in 0.5% SDS. 200 µg of the disrupted Ad5 vector or purified hexon or fiber is incubated with GNE (at several GNE to Ad capsomere molar ratios) overnight at 4° C. in PBS. Conjugates are characterized by SDS-PAGE, Western analysis with anti-adenovirus antibodies, and anti-cocaine antibodies.

Female Balb/c mice 4 to 6 weeks old and Wistar rats, 125-150 gm (Jackson Laboratory, Bar Harbor, Me. or Taconic, Germantown, N.Y.) are housed under pathogen-free conditions. The rodents are immunized with the conjugates by intramuscular injection. The conjugates are formulated in 5% lecithin polyacrylic adjuvant. The positive control is dAd5GNE (4 µg mice, 10 µg rats). Blood is collected from transected tail vein, centrifuged (10,000 g, 20 minutes), and serum stored at −20° C. Mice and rats will be immunized with the conjugates according to the prime-boost regimens outlined in Table 1 and Table 2, respectively.

TABLE 1

| Prime[1] | Boost (3 and 6 weeks) | Cocaine Dose (µg)[2] |
|---|---|---|
| A | B | 25, 50, 100 |
| C | D | 25, 50, 100 |
| E | F | 25, 50, 100 |
| G | H | 25, 50, 100 |
| dAd5GNE | dAd5GNE | 25, 50, 100 |
| Control (PBS) | Control (PBS) | 25, 50, 100 |
| Control (PBS) | Control (PBS) | None |

[1]A-H represent the best conjugate candidates/doses that will be chosen from titer, affinity, and blood-brain partition studies. These candidates include wild-type hexon, lysine-modified hexon, wild-type fiber, lysine-modified fiber, polymeric hexon, and polymeric fiber conjugates. The permutations include homologous prime boost and heterologous prime boost. Thus, prime boost can be component A followed by A (homologous) or component A followed by B (heterologous). Each comparison will include n = 10 Balb/c mice, vaccine administered IM.
[2]Behavior studies performed at 7 weeks post-primer administration using 25 µg cocaine IV 2x/week, then 50 µg 2x/week, then 100 µg 2x/week.

TABLE 2

| Prime[1] | Boost (3 and 6 weeks) | Cocaine Dose (mg/kg)[2] |
|---|---|---|
| A | B | 10, 15 |
| C | D | 10, 15 |
| dAd5GNE | dAd5GNE | 10, 15 |
| Control (PBS) | Control (PBS) | 10, 15 |
| Control (PBS) | Control (PBS) | None |

[1]A-D represent the four homologous and heterologous combinations of the two best vaccine candidates identified by the mouse hyperactivity studies (Table 1), e.g., prime-boost: vaccine 1-vaccine 1, vaccine 1-vaccine 2, vaccine 2-vaccine 1, vaccine 2-vaccine 2; n = 10 Wistar rats, vaccine administered IM.
[2]Behavior studies performed at 7 weeks post-primer administration during five days of cocaine sensitization in the locomotor cages. Cocaine challenges by IP, 10 mg/kg 2x/week for 2 weeks, then 15 mg/kg 2x/week for 2 weeks.

To assess anti-cocaine antibody levels and specificity, two-fold serial dilutions of serum are added to the wells of EIA/RIA plates, precoated with GNE-conjugated bovine serum albumin. GNE-specific IgG is probed with horseradish peroxidase conjugated goat anti-mouse IgG and detected with colorimetric peroxidase substrate. Anti-GNE antibody titers are calculated by interpolation of the log(OD)-log (dilution) with a cutoff value equal to 2-fold the absorbance of background.

To assess the cocaine blood/brain partition, nave and immunized mice are anesthetized by intraperitoneal injection of ketamine (100 mg/kg) and xylazine (10 mg/kg) two minutes prior to tail vein administration of 1.0 µCi [$^3$H] cocaine (PerkinElmer, Waltham, Mass.). One minute later, the mice are sacrificed and brain and trunk blood are collected separately. Cocaine concentration in brain, homogenized in PBS, and collected serum is quantified by scintillation counting. For the blood, cocaine is normalized to serum volume; for brain, cocaine is normalized to wet weight.

Mouse locomotor behavior is recorded using infrared beam-equipped activity open-field chambers (20 cm×20 cm chamber, Accuscan Instruments, Columbus, Ohio). At the same time of day for each assessment, mice are habituated for one hour prior to each test. Baseline behavior is recorded for 20 minutes, and the mice then receive PBS or cocaine (25, 50, or 100 µg, escalating dose each week) through the portal tail vein and returned to the chamber for 20 minutes. The highest dose (100 µg) is selected as this induces seizures in naïve mice.

Rat locomotor activity is performed in the same open field apparatus used with mice, but with 40 cm×40 cm chambers. Rats are habituated for 30 minutes before the cocaine injections, and analyzed for 30 minutes afterwards. Cocaine is administered by intraperitoneal (IP) injections at 10 or 15 mg/kg dose per rat. Rats are sensitized to cocaine through daily injections of cocaine for five days, and then challenged bi-weekly at the same dose for multiple weeks.

Cocaine self-administration, extinction, and reinstatement of responding for cocaine in rats is assessed by first catheterizing male Wistar rats (n=16) with indwelling catheters. After one week of recovery from surgery, the rats are trained to self-administer cocaine (0.5 mg/kg/injection) for one hour under a fixed-ratio (FR) schedule for at least one week and are allowed to self-administer cocaine under alternating FR and progressive-ratio (PR) schedules for another week (baseline). The rats are then divided into two groups (vaccine and PBS control), balanced by the number of injections per session during the last two FR and PR sessions. Rats will then be administered a prime and boosted three and five weeks later. The rats will be allowed to self-administer cocaine for two weeks under FR and PR schedules two weeks post priming, one week post first boost, and one week post second boost. Rats will then go through extinction sessions with the same conditions as the cocaine self-administration session except that a lever press does not deliver cocaine. Extinction sessions will last for a minimum of 10 days until responding decreases to less than 25% of cocaine self-administration. After extinction of responding, the rats will receive an injection of cocaine (0.5 mg/kg) immediately before a reinstatement session, and responding for cocaine will be measured under the same conditions as the extinction session. Vaccine duration may be evaluated by analysis at longer post immunization times. Over the course of the experiment, blood samples will be collected for the determination of anti-cocaine antibodies at the following timepoints: three weeks after the first immunization, one week after the second immunization, and after the reinstatement session. To control for any nonspecific effects or malaise, immunized animals are meal deprived and tested on a progressive ratio schedule for food reward. Vaccine efficacy can be further assessed by testing responding on extended access to cocaine (six hour access) over a 10-14 day period, where the vaccine may block the escalation in drug intake and the subsequent compulsive-like responding (see, e.g., Wee et al., Eur. Neuropsychopharmacol., 18: 303-311 (2008)).

The results of this example confirm the preparation of adenovirus coat protein-cocaine conjugates in accordance with the invention.

EXAMPLE 6

This example demonstrates that an adenovirus-antigen conjugate comprising a non-human primate adenovirus and a cocaine analog can induce an immune response against cocaine in mice.

Disrupted E1/E3-deleted adenoviral vectors based on human serotype 5 (dAd5GNE300), chimpanzee serotype C7 (dAdC7GNE300), and simian serotype 36 (dSAd36GNE300) were produced and coupled to GNE as described above. 4 µg of the resulting conjugates were separately injected intramuscularly to naïve Balb/c mice (n=5). Mice were boosted with the same adenoviral vector at 3 and 6 weeks post the initial priming injection. Total anti-GNE serum antibody titers were assessed by ELISA against BSA conjugated-GNC at various time points up to 12 weeks post prime. At all time points, the anti-cocaine antibody titers elicited by dAdC7GNE300 and dSAd36GNE300 were similar to the titers elicited by dAd5GNE300.

The results of this example demonstrate that a disrupted non-human primate adenovirus conjugated to a cocaine analog can induce antibody titers that are similar to those induced by a disrupted human adenovirus conjugated to the same cocaine analog.

EXAMPLE 7

This example describes a prime-boost method for inducing an immune response against cocaine in a mammal utilizing the conjugates described herein.

64 Balb/c mice will be primed and boosted with a dose of dAd5GNE or dsAd36GNE, which is a disrupted adenovirus-GNE conjugate based on sAd36, via intramuscular (IM) injection (see Table 3). Each of the experimental groups will be tested in naïve mice and in mice that have pre-existing Ad5 immunity.

TABLE 3

| Treatment Group[1] | Preimmune[2] | Prime | 1$^{st}$ Boost | 2$^{nd}$ Boost |
|---|---|---|---|---|
| 1 | No | dAd5GNE | dAd5GNE | dAd5GNE |
| 2 | No | dsAd36GNE | dsAd36GNE | dsAd36GNE |
| 3 | No | dAd5GNE | dsAd36GNE | dsAd36GNE |
| 4 | No | PBS | PBS | PBS |
| 5 | Yes | dAd5GNE | dAd5GNE | dAd5GNE |
| 6 | Yes | dsAd36GNE | dsAd36GNE | dsAd36GNE |
| 7 | Yes | dAd5GNE | dsAd36GNE | dsAd36GNE |
| 8 | Yes | PBS | PBS | PBS |

[1]Balb/c mice (n = 8) will be vaccinated IM with the lowest potent dose at 0, 3, and 6 weeks. Antibody titers will be assessed at 0, 2, 7, and 13 weeks by ELISA to GNE-conjugated BSA and (separately) GNE to Ad5. Competitive ELISA against GNE will be assessed at 13 weeks; blood/brain partition will be assessed as in Example 5.
[2]To develop immunity against Ad5, mice will be immunized with 2 × 10$^{10}$ particle units AdGFP, an E1$^-$E3$^-$ replication incompetent Ad5 expressing the GFP gene, at -10, -6, -2 weeks prior to the start of the study.

In addition to adenovirus-antigen conjugates, mice also will be immunized with conjugates comprising purified adenovirus capsid proteins and GNE. Hexon and fiber proteins will be produced as described in Example 5 from Ad5 and from sAd36. Using the two most potent capsid protein immunogens (with or without lysine modifications or crosslinks) identified in Example 5, similar immunogens will be constructed from the capsid proteins of sAd36. These will then be tested directly against the corresponding Ad5 capsid proteins, and in combination with the Ad5 capsid proteins, for the capacity to induce the highest titer and antibody affinity. 56 Balb/c mice will be primed and boosted with a dose of each of the adenovirus coat protein-antigen conjugates via IM injection as set forth in Table 4.

TABLE 4

| Treatment Group[1] | Prime | 1st Boost | 2nd Boost |
|---|---|---|---|
| 1 | Hexon (sAd36) | Hexon (sAd36) | Hexon (sAd36) |
| 2 | Hexon (Ad5) | Hexon (Ad5) | Hexon (Ad5) |
| 3 | Fiber (sAd36) | Fiber (sAd36) | Fiber (sAd36) |
| 4 | Fiber (Ad5) | Fiber (Ad5) | Fiber (Ad5) |
| 5 | Hexon (sAd36) | Hexon (Ad5) | Hexon (Ad5) |
| 6 | Fiber (Ad5) | Fiber (sAd36) | Fiber (sAd36) |
| 7 | PBS | PBS | PBS |

[1]Balb/c mice (n = 8) vaccinated IM with the lowest potent dose at 0, 3, and 6 weeks; antibody titers (ELISA) will be assessed at 0, 2, 7, and 13 weeks to GNE-conjugated BSA and separately to Ad5; a competitive ELISA against GNE will be assessed at 13 weeks.

The two best candidates from each of the studies outlined in Tables 3 and 4 will be tested for the ability to suppress cocaine-induced hyperlocomotor activity in mice in accordance with the regimen set forth in Table 5. Likewise, the two best candidates identified from the mouse hyperlocomotor activity assay will be tested for the ability to suppress cocaine-induced hyperlocomotor activity in rats according to the regimen set forth in Table 6.

TABLE 5

| Prime[1] | Boost (3 and 6 weeks) | Cocaine Dose (μg)[2] |
|---|---|---|
| A | B | 25, 50, 100 |
| C | D | 25, 50, 100 |
| E | F | 25, 50, 100 |
| G | H | 25, 50, 100 |
| Control (PBS) | Control (PBS) | 25, 50, 100 |
| Control (PBS) | Control (PBS) | None |

[1]A-H represent the best vaccine candidates/doses, with the best four chosen by titer/affinity and blood/brain partition studies of Ad5- or sAd36-based hexon, fiber, lysine-modified hexon or fiber, polymerized hexon or fiber, and disrupted Ad. The permutations include homologous prime-boost and heterologous prime-boost. Each assessment includes n = 10 Balb/c mice, IM vaccine.
[2]Behavior studies performed at 7 weeks post-primer administration. All behavior studies will include cocaine IV 25 μg 2x/wk, then 50 μg 2x/wk, then 100 μg 2x/wk.

TABLE 6

| Prime[1] | Boost (3 and 6 weeks) | Cocaine Dose (mg/kg)[2] |
|---|---|---|
| A | B | 10, 15 |
| C | D | 10, 15 |
| Control (PBS) | Control (PBS) | 10, 15 |
| Control (PBS) | Control (PBS) | None |

[1]A-D represent the best combinations from the mouse studies (Table 6); n = 10 Wistar rats
[2]Behavior studies performed at 7 weeks post-prime administration after 5 days of cocaine sensitization at 10 mg/kg. Cocaine administered IP, 10 mg/kg 2x/week for 2 weeks, then 15 mg/kg 2x/week for 2 weeks.

The two conjugate candidates that best suppress cocaine-induced hyperlocomotor activity in rats will then be assayed for the capacity to alter the cocaine self-administration behavior as described in Example 5.

The results of this example confirm that a method for inducing an immune response against an addictive drug in a mammal can be performed in accordance with the invention.

EXAMPLE 8

This example describes the preparation of an adeno-associated viral vector comprising a nucleic acid sequence that encodes an anti-cocaine antibody.

A nucleic acid sequence encoding the heavy chain of the anti-cocaine IgG monoclonal antibody GNC92H2 is followed by the furin 2A cleavage system (Fang et al., *Nat. Biotechnol.*, 23: 584-590 (2005)) and then the light chain of GNC92H2 is generated. The GNC92H2 monoclonal antibody was identified by screening GNC-(coupled to KLH) vaccinated mice (see, e.g., Carrera et al., *Proc. Natl. Acad. Sci. USA*, 98: 1988-1992 (2001)). GNC92H2 binds cocaine with high specificity and affinity ($K_d$ 2 nM), and functions in rat and mouse models of cocaine reinstatement and cocaine overdose prevention (Carrera et al., *Pharmacol. Biochem. Behav.*, 81: 709-714 (2005), and Carrera et al., *Proc. Natl. Acad. Sci. USA*, 98: 1988-1992 (2001)). GNC92H2 has higher specificity for cocaine as compared to the chemically-related major metabolites, benzoyl ecgonine and ecgonine methylester, by 2- and 4-orders of magnitude, respectively (Redwan et al., *Biotechnol. Bioeng.*, 82: 612-618 (2003)).

Genes are assembled by overlapping PCR using either cDNA- or *E. coli*-expressed variable domains as a template. The cDNAs are expressed from a CAG promoter in which the CMV enhancer and chicken β-actin promoter and intron are used with the rabbit β-globin splice acceptor and poly A site. Expression is confirmed by Western analysis following both native and reducing SDS/PAGE.

Antibody expression cassettes are placed between the inverted terminal repeats of adeno-associated virus serotype 2 in plasmids (see, e.g., Hildinger et al., *J. Virol.*, 75: 6199-6203 (2001)). The plasmids are co-transfected into 293 cells with a packaging plasmid having adenovirus helper functions, the rep gene from AAV2, and the cap gene from either AAVrh.10 or AAV 6.2, to produce AAVrh.10antiCoc and AAV6.2antiCoc. Pseudotyped AAV vectors are purified by iodixanol density gradient and ion exchange chromatography and characterized by physical titer (genome copies by TAQMAN™), purity (SDS-PAGE), sterility, absence of mycoloplasma and endotoxin, and in vitro gene transfer.

AAVrh.10antiCoc ($10^{11}$ genome copies) or AAVrh.10 GFP (control vector, GFP transgene) will be administered IV by tail vein to male BALB/c mice. In parallel, AAV6.2antiCoc, or separately AAV6.2GFP, will be administered to the nasal epithelium of male Balb/c mice. At 0, 2, and 4 weeks, anti-cocaine ELISA will be used to assay sera and nasal secretions. At 4 weeks the mice will be subject to blood/brain compartmentalization analysis with radiolabeled cocaine administered to the nasal cavity. The vector that provides the best protection as measured by the lowest brain levels of labeled cocaine will be tested further, either alone or in combination with one or more of the conjugates described in Examples 5 and 7, as set forth in Table 7.

TABLE 7

| Study[1] | Criteria | # of Test Groups | Treatment Parameters | Group Size |
|---|---|---|---|---|
| Mice locomotor activity | Suppression to normal ambulatory levels | 5 | best adenovirus-antigen conjugate or best coat protein-antigen conjugate from Examples 5 and 6, best AAV vector, best combination of conjugate + AAV | n = 10 |
| Rat locomotor activity | Suppression to normal ambulatory levels | 5 | same as above | n = 10 |
| Rat self-administration | Behavior consistent with suppression of cocaine-induced reward | 2 | best 2 conjugates/AAV or combinations thereof | n = 8 |

[1]The locomotor assays are done for all candidates; only the two candidates/combinations with the best results in locomotor assays will proceed to the self-administration study; negative controls for the conjugate vaccine are unconjugated protein or disrupted Ad, and for AAV vaccine the negative control is an AAV with irrelevant transgene; positive controls are the dAdGNE and AAVrh.10antiCoc alone or combined.

Each of the combinations set forth in Table 7 will be tested for the ability to suppress cocaine-induced hyperactivity in the mouse and rat models with increasing dose of cocaine challenge. The two combinations (or individual vaccine) that demonstrate complete suppression of cocaine-induced hyperactivity at the lowest dose of vaccine/highest dose of cocaine challenge will be compared in the rat self-administration assay. Of these two combinations (or individual vaccine), the one that demonstrates the greatest level of reward suppression will be the candidate developed for human clinical studies.

All data will be expressed as either geometric means (for serum titers) or means (behavior parameter) ±SEM. To assess these criteria with statistical certainty, existing data will be used to estimate the variance in experimental parameters. This variance is used for power calculations to determine the required number of animals per group. For titer measurements, data will be log transformed and treated as normally distributed with an observed variance of 0.4. This means use of n=8 per group allows observation of a 2-fold log difference between groups ($p<0.05$, power=0.95), corresponding to a 3-fold difference in titers. For behavioral assessments, (for example, ambulatory activity), variance is greater (2.0) and repeated measure ANOVA will be used for analysis of multiple cocaine challenges. Since the behavioral data is not normally distributed, statistical comparisons between the treated groups and controls will be conducted by non-parametric one-way ANOVA using the Kruskal-Wallis test, where the Kruskal-Wallis test uses mean score equal to the mean rank of each group, and the test statistic (H) being approximately chi-squared distributed. In the simplest experiments, a 2×3 design is used with two treatments (PBS or cocaine) and three groups (naive, disrupted Ad5GNE conjugate and new conjugate). Use of n=10 per group allows observation of a 2-fold difference in ambulatory activity ($p<0.05$, power=0.95). For self administration studies, the data will be expressed as the mean number of injections per session and mean mg/kg per session for each group of rats. Daily cocaine self-administration will be compared between experimental and control groups using a two-way repeated-measures ANOVA followed by the Bonferroni post hoc test (group×daily session; Prism 4.0, GraphPad). For extinction, responding per session will be compared between groups using a two-way repeated-measures ANOVA followed by the Bonferroni post hoc test (group× daily session). For reinstatement, responding per session will be compared between groups using a two-way repeated-measure ANOVA followed by the Bonferroni post hoc tests (group×priming drug). Locomotor activity will be compared using a two-way repeated-measures ANOVA followed by Bonferroni post hoc tests.

The results of this example confirms that an AAV vector encoding an anti-cocaine antibody can be generated and used to induce passive immunity against cocaine in a mammal.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of inducing an immune response against an addictive drug in a mammal, which method comprises:
   (a) preparing a replication-deficient adenovirus comprising an adenoviral genome except for all or part of the E1A region, all or part of the E1B region, and all or part of the E3 region of the adenoviral genome,
   (b) exposing the adenovirus to a temperature of about 50° C. to 70° C. and treating the adenovirus with sodium dodecyl sulfate (SDS) to release the nucleoprotein core and capsid proteins of the adenovirus,
   (c) covalently linking an antigen of an addictive drug to one or more of the adenovirus capsid proteins to produce an adenovirus-antigen conjugate, thereby producing a composition comprising the adenovirus nucleoprotein core and the adenovirus-antigen conjugate, wherein the composition does not contain an intact adenovirus particle, and
   (d) administering the composition to a mammal, whereby the antigen is presented to the immune system of the mammal to induce an immune response against the antigen in the mammal.

2. The method of claim 1, wherein the antigen is an addictive drug or an analog or portion thereof.

3. The method of claim 1, wherein the antigen is a small molecule.

4. The method of claim 3, wherein the small molecule is a hapten.

5. The method of claim 1, wherein the one or more capsid proteins is a hexon protein, a fiber protein, or a penton base protein.

6. The method of claim 1, wherein the capsid protein comprises at least one non-native lysine residue.

7. The method of claim 6, wherein the capsid protein comprises 5 to 10 non-native lysine residues.

8. The method of claim 2, wherein the addictive drug is selected from the group consisting of opioids, morphine derivatives, depressants, dissociative anesthetics, cannabinoids, hallucinogens, stimulants, prescription medications, anabolic steroids, inhalants, and club drugs.

9. The method of claim 2, wherein the addictive drug is selected from the group consisting of cocaine, fentanyl, heroin, morphine, opium, oxycodone, hydrocodone, ketamine, phencyclidine (PCP), barbiturates, benzodiazepines, flunitrazepam, y-hydroxybutyric acid (GHB), methaqualone, hashish, marijuana, lysergic acid diethylamide (LSD), mescaline, psilocybin, amphetamine, 3.4-Methylenedioxymethamphetamine (MDMA), methamphetamine, methylphenidate, and nicotine.

10. The method of claim 9, wherein the addictive drug is cocaine.

11. The method of claim 1, wherein the antigen is 6-(2R, 3S)-3-(benzoyloxy)-8-methyl-8-azabicyclo [3.2.1]octane-2-carbonyloxy-hexanoic acid (GNC) or 6-((2R,3S)-3-(benzoyloxy)-8-methyl-8-azabicyclo [3.2.1] octane-2-carboxamido)hexanoic acid) (GNE).

12. The method of claim 1, wherein the immune response induced against the addictive drug in the mammal by administration of the composition is greater than the immune response induced in the mammal by administration of the antigen alone.

13. The method of claim 1, wherein the replication-deficient adenovirus is a human or non-human primate adenovirus.

14. The method of claim 13, wherein the replication-deficient adenovirus is a human serotype 5 adenovirus.

15. The method of claim 13, wherein the adenovirus is a non-human primate serotype C7 or sAd36 adenovirus.

* * * * *